(12) United States Patent
Motorykin et al.

(10) Patent No.: US 12,222,354 B2
(45) Date of Patent: Feb. 11, 2025

(54) IDENTIFICATION AND QUANTITATION OF INSULIN-LIKE GROWTH FACTOR-I VARIANTS BY MASS SPECTROMETRY

(71) Applicant: Quest Diagnostics Investments LLC, Secaucus, NJ (US)

(72) Inventors: Ievgen Motorykin, Carlsbad, CA (US); Nigel Clarke, San Clemente, CA (US); Michael J. McPhaul, Capistrano Beach, CA (US); Zengru Wu, Ladera Ranch, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 354 days.

(21) Appl. No.: 17/697,813

(22) Filed: Mar. 17, 2022

(65) Prior Publication Data
US 2022/0299524 A1    Sep. 22, 2022

Related U.S. Application Data

(60) Provisional application No. 63/163,502, filed on Mar. 19, 2021.

(51) Int. Cl.
*G01N 33/68* (2006.01)
*G01N 33/74* (2006.01)

(52) U.S. Cl.
CPC ......... *G01N 33/6848* (2013.01); *G01N 33/74* (2013.01)

(58) Field of Classification Search
CPC ..................... G01N 33/6848; G01N 33/74
See application file for complete search history.

(56) References Cited

U.S. PATENT DOCUMENTS

| | | | |
|---|---|---|---|
| 11,454,637 B2 * | 9/2022 | Bystrom | ............... G01N 33/74 |
| 2006/0154865 A1 | 7/2006 | Amrein et al. | |
| 2008/0064044 A9 | 3/2008 | Nelson et al. | |
| 2021/0041462 A1 | 2/2021 | Bystrom et al. | |

FOREIGN PATENT DOCUMENTS

| | | |
|---|---|---|
| JP | 2010535507 A | 11/2010 |
| WO | 2006026717 A2 | 3/2006 |
| WO | 2010093820 A2 | 8/2010 |
| WO | 2011057021 A1 | 5/2011 |

OTHER PUBLICATIONS

Bredehoft M., et al., "Quantification of Human Insulin-Like Growth Factor-1 and Qualitative Detection of Its Analogues in Plasma Using Liquid Chromatography/Electrospray Ionisation Tandem Mass Spectrometry," Rapid Communications in Mass Spectrometry, 2008, vol. 22 (4), pp. 477-485.
International Search Report and Written Opinion for Application No. PCT/US2022/020906, mailed on Jun. 30, 2022.

(Continued)

*Primary Examiner* — Nicole M Ippolito
*Assistant Examiner* — Hanway Chang
(74) *Attorney, Agent, or Firm* — Foley & Lardner LLP

(57) ABSTRACT

Methods are provided for detecting insulin-like growth factor-I (IGF-I) variant(s) in a sample. Methods provided herein are further directed to using the detected ion or ions to determine the presence of IGF1 variant(s) in the sample.

7 Claims, 11 Drawing Sheets

(56) References Cited

OTHER PUBLICATIONS

Kam et al., "Serum Insulin-like Growth Factor I Quantitation by Mass Spectrometry: Insights for Protein Quantitation With This Technology, "EJIFCC, Dec. 2016, vol. 27 (4), pp. 318-330.
Motorykin et al., "Isotopic Peak Index, Relative Retention Time, and Tandem MS for Automated High Throughput IGF-1 Variants Identification in a Clinical Laboratory," Analytical Chemistry, Aug. 2021, vol. 93 (34), pp. 11836-11842.
Wu et al., "Detection of Insulin-like Growth Factor 1 Variants by Mass Spectrometry: Results From a Clinical Reference Laboratory," Clinical Chemistry, Aug. 2019, vol. 65 (8), pp. 1060-1061.
International Preliminary Report on Patentability for International Application No. PCT/US2022/020906 mailed on Sep. 28, 2023.
International Search Report and Written Opinion for Application No. PCT/US2023/017873, mailed on Jul. 17, 2023.

\* cited by examiner

A     Variant Report

Sample ID: 604306430049     Instrument ID   07322L    Method    MM IGF-1 9STDS
Date:    1/5/2021 9:06:26 AM     Batch name    0103F078R Vial Pos.   CStk1-02:49
VG4: R-W, V-M, T-M, A-T, S-N, A-P, A-V, M-R    m/z 1098.0969

B     IGF-1 Quantitation report

Sample: 503328440016                                 Vial #: CStk1-01:16
Date: 1/5/2021 10:47                                  Batch: 1103F019

Quant m/z: 1093.5215    Qual 1 m/z: 1093.3782    Qual 2 m/z: 1093.6648    ISTD m/z: 1106.7699

| | Response | RT | Ion Ratio Range | | Ion Ratio | Final Result |
|---|---|---|---|---|---|---|
| Quant | 69,406 | 0.34 | | | | |
| Qual 1 | 73,651 | 0.34 | 64.50% | 104.50% | 106.12% | 4 ng/mL |
| Qual 2 | 165,054 | 0.36 | 88.40% | 128.40% | 237.81% | |
| ISTD | 4,357,419 | 0.34 | | | | |

Sample Type: Specimen                      Integration Method    POSSIBLE HOMO VAR

IDENTIFICATION AND QUANTITATION OF INSULIN-LIKE GROWTH FACTOR-I VARIANTS BY MASS SPECTROMETRY

CROSS REFERENCE TO RELATED PATENT APPLICATIONS

This application claims priority to U.S. Provisional Application. No. 63/163,502, filed Mar. 19, 2021, the contents of which are hereby incorporated by reference in their entirety.

FIELD OF THE INVENTION

The invention relates to the identification and quantitation of insulin-like growth factor 1 variants using mass spectrometry.

BACKGROUND OF THE INVENTION

IGF-I is a hormone with a molecular structure similar to insulin. It is a peptide produced by the liver and contains 70 amino acids in a single chain with three intramolecular disulfide bridges. IGF-I has a molecular weight of about 7,649 Da and is highly protein bound in serum. Production is stimulated by growth hormone and can be retarded by undernutrition, growth hormone insensitivity, lack of growth hormone receptors, or failure of a downstream signaling pathway. IGF-I plays an important role in childhood growth and continues to have anabolic effects in adults.

The high-resolution LC-MS based approach is effective for quantitation of peptides in specimens from most patients; however amino acid substitutions due to polymorphisms can lead to changes in mass, essentially "hiding" the polymorphic variant. The possibility of having polymorphisms increases when larger polypeptides with more amino acid residues are monitored.

Because protein quantitation is based on peak intensity at a specific mass-to-charge ratio (m/z) of the wild type (WT) protein, the IGF-1 quantitation only includes the WT and does not include polymorphisms. For example, the presence of IGF-1 variants may indicate that the WT concentration only represents half the circulating IGF-1 for heterozygous individuals, or the absence of wild type IGF-1 may be explained by the individual being homozygous for a variant or heterozygous for 2 different variants. Some variants are reported to be pathogenic, while most others have unclear clinical significance. This information is important for clinicians when interpreting IGF-1 test results for their patients. In addition, knowing what variants are present in patients with specific phenotypes will help expand our understanding of genotype-phenotype relationships and their clinical significance.

An effective method for identifying IGF-1 variants is needed.

SUMMARY OF THE INVENTION

The methods provided herein comprise Isotopic Peak Index (ISI), which allows simultaneous monitoring of 15 IGF-1 variants by using 4 m/z ratios. Also provided herein is a Relative Retention Time (RRT) parameter that allows distinction of previously unresolved variants. Also provided herein is a method utilizing tandem mass spectrometry (MS/MS) to distinguish between the most common pair of variants: isobaric A67T and A70T.

The methods described herein comprise enhanced automation, avoiding detailed manual calculations that are prone to human error, and the ability to monitor more, and discover new, IGF-1 variants. This approach identified 6 variants from the ExAC database: P66A, A67S, S34N, A38V, A67T, and A70T; 2 previously reported V44M and A67V variants; and discovered 6 unreported variants: Y31H, S33P, R50Q, R56K, T41I, and A62T. The methods provided herein comprise a profile of patient's IGF-1 status and can be used to explore genotype-phenotype relationships in IGF-1 variants.

The methods described herein are for simultaneously monitoring 15 IGF-1 variants in groups using 4 mass/charge (m/z) ratios, without compromising quantitation of the WT. Most variants within each group are distinguished by their isotopic distribution and relative retention times, while reanalysis by MS/MS distinguishes A67T from A70T. Calculations and interpretation of LC-MS data are automated using commercial instrument software, with very little need for operator intervention, thus protecting the workflow from human error in interpretation of results.

In some embodiments, methods comprise detecting the following mass/charge (m/z) ratios for each of the variants of interest:

| Group | m/z | Variant Peaks Covered |
|---|---|---|
| WT | 1093.52149 | $WT_4$, $P66T_1$ |
| VG1 | 1089.80497 | $P66A_4$, $R55K_6$, $R36Q_6$ |
| VG2 | 1095.80648 | $A67S_4$, $T29I_8$ |
| VG3 | 1097.09596 | $S34N_2$, $A70P_3$, $A38V_1$, $M59R_4$, $A67S_{13}$ |
| VG4 | 1098.09687 | $S34N_9$, $A70P_{10}$, $A38V_8$, $M59R_{11}$, $V17/44M_4$, $R50W_6$, $T4M_6$, $A67/70T_6$ |

In some embodiments, methods provided herein are methods for detecting insulin-like growth factor-I (IGF-I) variant(s) in a sample, the method comprising: ionizing IGF-I in the sample to produce one or more ions detectable by mass spectrometry; detecting one or more of the ions comprising an ion with a mass-to-charge ratio selected from the group consisting of 1093.5±0.5, 1089.8±0.5, 1095±0.5, 1097.09±0.5, 1098.09±0.5, by mass spectrometry; and using the detected ion or ions to determine the presence of IGF1 variant(s) in the sample.

In some embodiments, detection of m/z 1093.5±0.5 determines the presence of $WT_4$ or $P66T_1$.

In some embodiments, detection of m/z 1089.8±0.5 determines the presence of $P66A_4$, $R55K_6$, or $R36Q_6$.

In some embodiments, detection of m/z 1095.8±0.5 determines the presence of $A67S_4$ or $T29I_8$.

In some embodiments, detection of m/z 1097.09±0.5 determines the presence of $S34N_2$, $A70P_3$, $A38V_1$, $M59R_4$, or $A67S_{13}$.

In some embodiments, detection of m/z 1098.09±0.5 determines the presence of $S34N_9$, $A70P_{10}$, $A38V_8$, $M59R_{11}$, $V17/44M_4$, $R50W_6$, $T4M_6$, or $A67/70T_6$.

In some embodiments, methods provided herein comprise purifying the protein by high performance liquid chromatography (HPLC) prior to ionization.

In some embodiments, wherein the sample comprises plasma or serum.

In some embodiments, the sample may be purified by high performance liquid chromatography (HPLC) prior to ionization. In related embodiments, IGF-1 and its variants are extracted and resolved using a multiplex high performance liquid chromatography (HPLC) system (Aria TLX-4) equipped with an on-line extraction.

In some embodiments, the sample may be purified by solid phase extraction (SPE) prior to ionization.

In some embodiments, the mass spectrometry comprises Q Exactive Focus Hybrid Quadrupole-Orbitrap instrument.

In some embodiments, the high resolution/high accuracy mass spectrometry is conducted with a resolving power (FWHM) of greater than or equal to about 10,000, such as greater than or equal to about 15,000, such as greater than or equal to about 20,000, such as greater than or equal to about 25,000. In some embodiments, the high resolution/high accuracy mass spectrometry is conducted at an accuracy of less than or equal to about 50 ppm, such as less than or equal to about 20 ppm, such as less than or equal to about 10 ppm, such as less than or equal to about 5 ppm; such as less than or equal to about 3 ppm. In some embodiments, high resolution/high accuracy mass spectrometry is conducted at a resolving power (FWHM) of greater than or equal to about 10,000 and an accuracy of less than or equal to about 50 ppm. In some embodiments, the resolving power is greater than about 15,000 and the accuracy is less than or equal to about 20 ppm. In some embodiments, the resolving power is greater than or equal to about 20,000 and the accuracy is less than or equal to about 10 ppm; preferably resolving power is greater than or equal to about 25,000 and accuracy is less than or equal to about 5 ppm, such as less than or equal to about 3 ppm.

In some embodiments, the high resolution/high accuracy mass spectrometry may be conducted with an orbitrap mass spectrometer, a time of flight (TOF) mass spectrometer, or a Fourier transform ion cyclotron resonance mass spectrometer (sometimes known as a Fourier transform mass spectrometer). In some embodiments, the sample may include a biological sample; preferably plasma or serum.

In some embodiments, relating the amount of one or more IGF-I ions detected by mass spectrometry to the amount of an IGF-I protein in the sample includes comparison to an internal standard; such as a human or non-human IGF-I protein (e.g., intact recombinant mouse recombinant mouse IGF-I). The internal standard may optionally be isotopically labeled.

The features of the embodiments listed above may be combined without limitation for use in methods of the present invention.

In certain preferred embodiments, mass spectrometry is performed in positive ion mode. Alternatively, mass spectrometry is performed in negative ion mode. The preferred ionization technique used in methods described herein is electrospray ionization (ESI). Electrospray ionization may be conducted, for example, with a heated ionization source. In some embodiments, methods provided herein comprise heated electrospray ionization (HESI). In some embodiments, methods provided herein comprise heated electrospray ionization (HESI) in positive ion mode.

In preferred embodiments, one or more separately detectable internal standards is provided in the sample, the amount of which is also determined in the sample. In these embodiments, all or a portion of both the analyte of interest and the one or more internal standards is ionized to produce a plurality of ions detectable in a mass spectrometer, and one or more ions produced from each are detected by mass spectrometry. The internal standards may be selected from the group consisting of intact non-human IGF-I (e.g., isotopically labeled or unlabeled intact recombinant mouse IGF-I), an isotopically labeled intact human IGF-I protein.

In other embodiments, the amount of an intact IGF-I protein in a sample may be determined by comparison to one or more external reference standards. Exemplary external reference standards include blank plasma or serum spiked with an isotopically labeled or unlabeled, intact human or non-human IGF-I (e.g., isotopically labeled or unlabeled intact recombinant mouse IGF-I).

In some embodiments, an isotopic signature comprising mass spectrometric peaks from two or more molecular isotopic forms of an analyte may be used to confirm the identity of an analyte being studied. In other embodiments, a mass spectrometric peak from one or more isotopic forms may be used to quantitate the analyte of interest. In some related embodiments, a single the mass spectrometric peak from one isotopic form may be used to quantitate an analyte of interest. In other related embodiments, a plurality of isotopic peaks may be used to quantitate an analyte. The plurality of peaks may be subject to any appropriate mathematical treatment. Several mathematical treatments are known in the art and include, but are not limited to, summing the area under multiple peaks, or averaging the response from multiple peaks.

As used herein, unless otherwise stated, the singular forms "a," "an," and "the" include plural reference. Thus, for example, a reference to "a protein" includes a plurality of protein molecules.

As used herein, the term "IGF-I protein" refers to full-length IGF-I polypeptides or fragments thereof, as well as full-length IGF-I variant polypeptides or fragments thereof. IGF-I variants include, for example, long R3 IGF-I, which is an 83 amino acid analog of IGF-I comprising the complete human IGF-I sequence with the substitution of an Arg(R) for the Glu(E) at position three (hence R3) and a 13 amino acid extension peptide at the N terminus. This analog of IGF-I has been produced with the purpose of increasing the biological activity of the IGF-I peptide. The mass of this analog is about 9111.4 Daltons, thus multiply charged long R3 IGF-I ions may be observed with m/z ratios of about 1014.1±1, 1140.7±1, 1303.5±1, and 1520.6±1. Other IGF-I variant polypeptides are readily recognized by one of skill in the art, including for example full-length IGF-I polypeptides or fragments thereof that have been chemically modified. Exemplary chemical modifications may include reduction of one or more disulfide bridges or alkylation of one or more cystines. These exemplary chemical modifications result in an increase in the mass of an IGF-I variant polypeptide relative to the mass of the corresponding unmodified IGF-I polypeptide. Reduction of one or more disulfide bridges results in a relatively minor change in the mass of the molecule, with the resulting mass to charge ratios falling within the mass to charge ratio ranges described herein. Other chemical modifications that result in a mass deviation from an unmodified IGF-I polypeptide are also encompassed within the meaning of IGF-I protein. One skilled in the art understands that the addition of atoms to an IGF-I protein by chemical modification will result in an observed increase in the mass to charge ratios during mass spectrometry. Thus, IGF-I protein variants that result from chemical modification are included within the meaning IGF-I protein and detectable in accordance with the methods of the invention.

As used here, the term "intact" as describing a polypeptide refers to the full-length (i.e., unfragmented) polypeptide. Intact IGF-I, for example, is a polypeptide containing 70 amino acid residues, and intact long R3 IGF-I is an 83 amino acid analog of IGF-I comprising the complete human IGF-I sequence with the substitution of an Arg(R) for the GLu(E) at position three (hence R3) and a 13 amino acid extension peptide at the N terminus. Non-intact forms of IGF-I (i.e., fragments) may also be detected by the methods described herein. For example, fragments of IGF-I proteins with a molecular weight of about 1,000 Daltons or larger, such as about 1500 Daltons or larger, such as about 2000

Daltons or larger, such as about 2500 Daltons or larger, such as about 3000 Daltons or larger, such as about 4000 Daltons or larger, such as about 5000 Daltons or larger, such as about 6000 Daltons or larger, such as about 7000 Daltons or larger may be detected by methods described herein.

The term "purification" or "purifying" refers to a procedure that enriches the amount of one or more analytes of interest relative to other components in the sample that may interfere with detection of the analyte of interest. Although not required, "purification" may completely remove all interfering components, or even all material other than the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

The term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In preferred embodiments, the sample comprises a body fluid sample; preferably plasma or serum.

The term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE may operate via a unitary or mixed mode mechanism. As used herein, SPE can be conducted with an extraction column or cartridge such as, for example, a turbulent flow liquid chromatography (TFLC) column. Mixed mode mechanisms utilize ion exchange and hydrophobic retention in the same column; for example, the solid phase of a mixed-mode SPE column may exhibit strong anion exchange and hydrophobic retention; or may exhibit strong cation exchange and hydrophobic retention.

The term "chromatography" refers to a process in which a chemical mixture carried by a liquid or gas is separated into components as a result of differential distribution of the chemical entities as they flow through a stationary solid phase.

The term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of separation techniques which employ "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography). In some embodiments, an SPE column may be used in combination with an LC column. For example, a sample may be purified with a TFLC extraction column, followed by additional purification with a HPLC analytical column.

The term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

The term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow, the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

The term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

The terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

The term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, "high resolution/high accuracy mass spectrometry" refers to mass spectrometry conducted with a mass analyzer capable of measuring the mass to charge ratio of a charged species with sufficient precision and accuracy to confirm a unique chemical ion. Confirmation of a unique chemical ion is possible for an ion when individual isotopic peaks from that ion are readily discernable. The particular resolving power and mass accuracy necessary to confirm a unique chemical ion varies with the mass and charge state of the ion.

As used herein, the term "resolving power" or "resolving power (FWHM)" (also known in the art as "$m/\Delta m_{50\%}$") refers to an observed mass to charge ratio divided by the width of the mass peak at 50% maximum height (Full Width Half Maximum, "FWHM"). The effect of differences in resolving power is illustrated in FIGS. 1A-C, which show theoretical mass spectra of an ion with a m/z of about 1093. FIG. 1A shows a theoretical mass spectrum from a mass analyzer with resolving power of about 3000 (a typical operating condition for a conventional quadrupole mass analyzer). As seen in FIG. 1A, no individual isotopic peaks are discernable. By comparison, FIG. 1B shows a theoretical mass spectrum from a mass analyzer with resolving power of about 10,000, with clearly discernable individual isotopic peaks. FIG. 1C shows a theoretical mass spectrum from a mass analyzer with resolving power of about 12,000. At this highest resolving power, the individual isotopic peaks contain less than 1% contribution from baseline.

As used herein a "unique chemical ion" with respect to mass spectrometry refers a single ion with a single atomic makeup. The single ion may be singly or multiply charged.

As used herein, the term "accuracy" (or "mass accuracy") with respect to mass spectrometry refers to potential deviation of the instrument response from the true m/z of the ion investigated. Accuracy is typically expressed in parts per million (ppm). The effect of differences in mass accuracy is illustrated in FIGS. 2A-D, which show the boundaries of potential differences between a detected m/z and the actual m/z for a theoretical peak at m/z of 1093.52094. FIG. 2A shows the potential range of detected m/z at an accuracy of 120 ppm. By contrast, FIG. 2B shows the potential range of detected m/z at an accuracy of 50 ppm. FIGS. 2C and 2D show the even narrower potential ranges of detected m/z at accuracies of 20 ppm and 10 ppm.

High resolution/high accuracy mass spectrometry methods of the present invention may be conducted on instruments capable of performing mass analysis with FWHM of greater than 10,000, 15,000, 20,000, 25,000, 50,000, 100,000, or even more. Likewise, methods of the present invention may be conducted on instruments capable of performing mass analysis with accuracy of less than 50 ppm, 20 ppm, 15 ppm, 10 ppm, 5 ppm, 3 ppm, or even less. Instruments capable of these performance characteristics may incorporate certain orbitrap mass analyzers, time-of-flight ("TOF") mass analyzers, or Fourier-transform ion cyclotron resonance mass analyzers. In preferred embodiments, the methods are carried out with an instrument which includes an orbitrap mass analyzer or a TOF mass analyzer.

The term "orbitrap" describes an ion trap consisting of an outer barrel-like electrode and a coaxial inner electrode. Ions are injected tangentially into the electric field between the electrodes and trapped because electrostatic interactions between the ions and electrodes are balanced by centrifugal forces as the ions orbit the coaxial inner electrode. As an ion orbits the coaxial inner electrode, the orbital path of a trapped ion oscillates along the axis of the central electrode at a harmonic frequency relative to the mass to charge ratio of the ion. Detection of the orbital oscillation frequency allows the orbitrap to be used as a mass analyzer with high accuracy (as low as 1-2 ppm) and high resolving power (FWHM) (up to about 200,000). A mass analyzer based on an orbitrap is described in detail in U.S. Pat. No. 6,995,364, incorporated by reference herein in its entirety. Use of orbitrap analyzers has been reported for qualitative and quantitative analyses of various analytes. See, e.g., U.S. Patent Application Pub. No. 2008/0118932 (filed Nov. 9, 2007); Bredehöft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

The term "operating in negative ion mode" refers to those mass spectrometry methods where negative ions are generated and detected. The term "operating in positive ion mode" as used herein, refers to those mass spectrometry methods where positive ions are generated and detected.

The term "ionization" or "ionizing" refers to the process of generating an ion having a net electrical charge equal to one or more electron units. Negative ions are those having a net negative charge of one or more electron units, while positive ions are those having a net positive charge of one or more electron units.

The term "selective ion monitoring" is a detection mode for a mass spectrometric instrument in which only ions within a relatively narrow mass range, typically about one mass unit or less, are detected.

"Multiple reaction mode," sometimes known as "selected reaction monitoring," is a detection mode for a mass spectrometric instrument in which a precursor ion and one or more fragment ions are selectively detected.

The terms "lower limit of quantification", "lower limit of quantitation" or "LLOQ" refer to the point where measurements become quantitatively meaningful. The analyte response at this LLOQ is identifiable, discrete and reproducible with a relative standard deviation (RSD %) of less than 20% and an accuracy of 85% to 115%.

The term "limit of detection" or "LOD" is the point at which the measured value is larger than the uncertainty associated with its measurement. The LOD is defined as four times the RSD of the mean at the zero concentration.

The term "simultaneous" as applied to simultaneously detecting the amount of two or more analytes from a sample means acquiring data reflective of the amount of the two or more analytes in the sample from the same sample injection. The data for each analyte may be acquired sequentially or in parallel, depending on the instrumental techniques employed. For example, a single sample containing two analytes, such as intact IGF-I and IGF-II proteins, may be injected into a HPLC column, which may then elute each analyte one after the other, resulting in introduction of the analytes into a mass spectrometer sequentially. Determining the amount of each of these two analytes is simultaneous for the purposes herein, as both analytes result from the same sample injection into the HPLC.

An "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

DETAILED DESCRIPTION OF THE INVENTION

Figure 1:
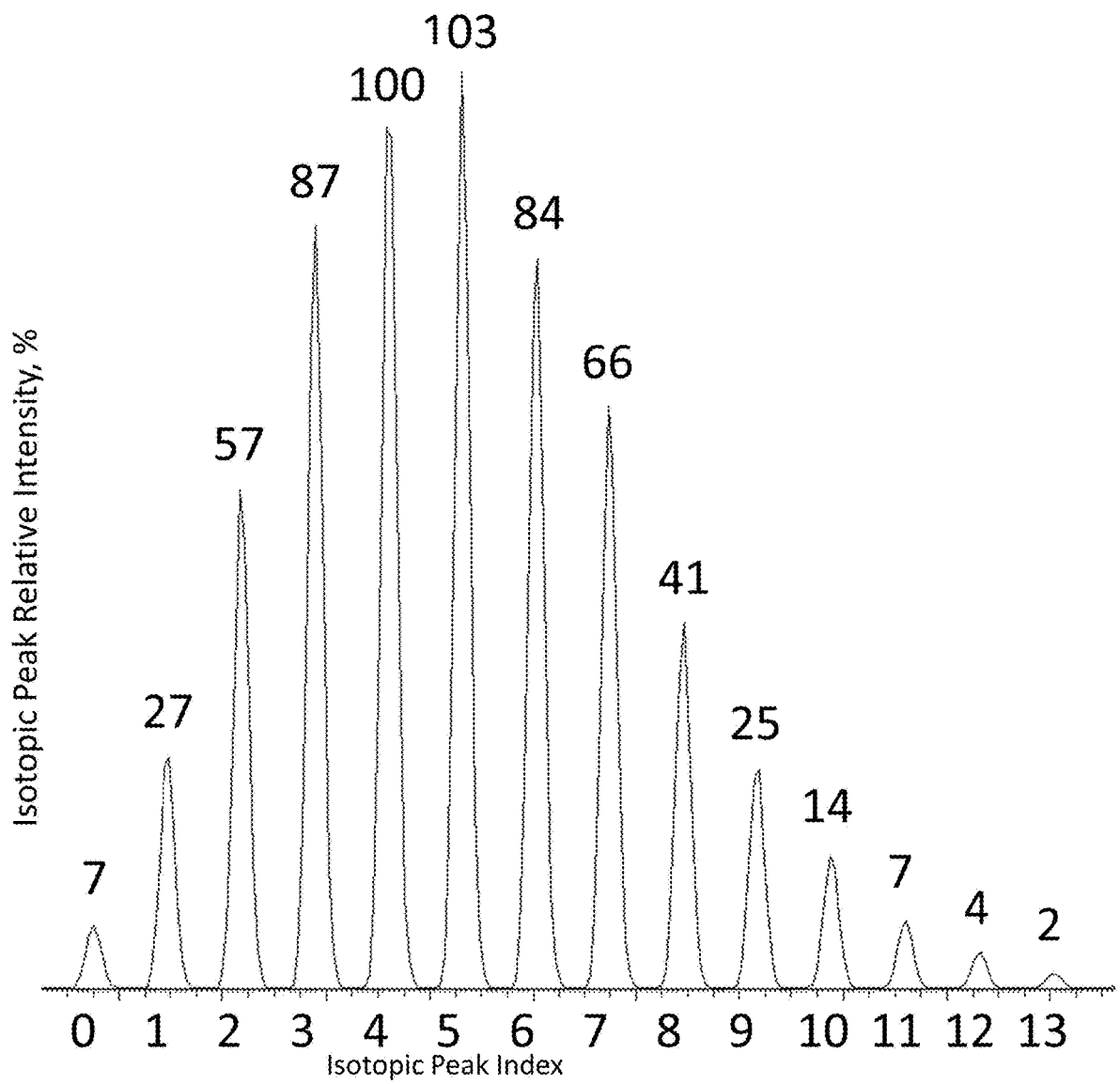
FIG. 1 shows the principle of the $IP_i$ concept, in which Isotopic Peak Index is bound to Isotopic Peak relative Intensity. In any charge state, the IGF-1 WT and all variants will follow this Index-Intensity distribution. The IPrI is calculated relative to the intensity of the IP4 peak as it is used for the quantitation of the WT IGF-1.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition.

Quality control (QC) pools having known concentrations, for use in embodiments of the present invention, are preferably prepared using a matrix similar to the intended sample matrix.

Sample Preparation for Mass Spectrometric Analysis

In preparation for mass spectrometric analysis, an IGF-I protein may be enriched relative to one or more other components in the sample (e.g. other proteins) by various methods known in the art, including for example, solid phase extraction (SPE), LC, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like. In some embodiments, liquid chromatography and/or SPE, and/or protein precipitation may be used in combination.

Protein precipitation is one method of preparing a test sample, especially a biological sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving IGF-I and/or IGF-II proteins in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to solid phase extraction and/or liquid chromatography and subsequent mass spectrometry analysis. In certain embodiments, the use of protein precipitation such as for example, acid ethanol protein precipitation, may obviate the need for TFLC, SPE, or other on-line extraction prior to mass spectrometry or HPLC and mass spectrometry.

In preferred embodiments, liquid-liquid extraction methods (such as acid ethanol extraction) are used to extract native intact IGF-I and/or IGF-II from a sample. In these embodiments, between 10 μl and 500 μl of sample, such as between 25 μl and 250 μl, such as about 100 μl, is added to a portion of extraction solvent. The quantity of extraction solvent is commensurate with sample volume and may vary depending on the extraction solvent used, but is preferably between about 50 μl and 1000 μl. The sample/solvent mixtures are mixed and centrifuged, and a portion of the supernatant or organic phase (depending on solvent used) is drawn off for further analysis. Solvent may be removed from the drawn off portion, for example under a nitrogen flow, and the residue reconstituted in a different solvent from that used for the liquid-liquid extraction. At least a portion of the resulting solution may then be subjected to additional processing steps, such as SPE and/or LC, prior to mass spectrometry.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with IGF-I and/or IGF-II. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In preferred embodiments, the column is a C-18 alkyl bonded column (such as a Phenomenex Onyx monolithic C-18 column). The chromatographic column includes an inlet port for receiving a sample and an outlet port for discharging an effluent that includes the fractionated sample. The sample may be supplied to the inlet port directly, or from a SPE column, such as an on-line SPE guard cartridge or a TFLC column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In some embodiments, HPLC is conducted with an alkyl bonded analytical column chromatographic system. In certain embodiments, a C-18 analytical column (e.g., Phenomenex Onyx Monolithic C18, or equivalent) is used. In certain embodiments, HPLC and/or TFLC are performed using HPLC Grade 0.2% formic acid in water as mobile phase A and 0.2% formic acid in acetonitrile as mobile phase B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of an IGF-I protein or fragment prior to mass spectrometry. In such embodiments, samples may be extracted using a TFLC column which captures the analyte, then eluted and chromatographed on a second TFLC column or on an analytical HPLC column prior to ionization. For example, sample extraction with a TFLC extraction column may be accomplished with a large particle size (50 μm) packed column. Sample eluted off of this column may then be transferred to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, protein precipitation is accomplished with acid ethanol extraction from serum, and the resulting solution is subjected to SPE, preferably conducted on-line with a C-18 extraction column (e.g., a Phenomenex Onyx C-18 guard cartridge, or equivalent). The eluent from the SPE column may then be applied to an analytical LC column, such as a HPLC column in an on-line fashion, prior to mass spectrometric analysis.

Detection and Quantitation by Mass Spectrometry

Mass spectrometry is performed using a mass spectrometer, which includes an ion source for ionizing a sample and creating charged molecules for further analysis. In various embodiments, an IGF-I and/or IGF-II protein may be ionized by any suitable method known to the skilled artisan. For example, ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc. Depending on the particular ionization method and conditions employed, IGF-I and IGF-II proteins may be ionized to a number of different charge states. The ionization source may be selected to minimize the dispersion of charge states generated. In some embodiments, ESI (optionally heated) is used as the ionization source, and the ionization conditions are optimized to minimize the disbursement of observed multiply charged IGF-I and/or IGF-II protein ions.

IGF-I and/or IGF-II proteins may be ionized in positive or negative mode. In preferred embodiments, one or more IGF-I and/or IGF-II proteins are ionized in positive mode. In some embodiments, multiply charged intact IGF-I ions are generated with m/z ratios within the ranges of about 850.8±2, 957.1±2, 1093.7±2, and 1275.8±2. In some embodiments, multiply charged intact IGF-II ions are generated with m/z ratios within the ranges of about 934.69±2, 1068.07±2, 1245.92±2, and 1494.89±2. The majority of the generated multiply charged ions within these ranges may fall within a narrower sub-range, such as the indicated m/z±1.

In mass spectrometry techniques generally, after the sample has been ionized, the positively or negatively charged ions thereby created may be analyzed to determine a mass to charge ratio (m/z). Various analyzers for determining m/z include quadrupole analyzers, ion trap analyzers, and time-of-flight analyzers, and orbitrap analyzers. According to methods of the present invention, high resolution/high accuracy mass spectrometry is used for quantitative analysis of IGF-I and/or IGF-II proteins. That is, mass spectrometry is conducted with a mass spectrometer capable of exhibiting a resolving power (FWHM) of at least 10,000, with accuracy of about 50 ppm or less for the ions of interest; preferably the mass spectrometer exhibits a resolving power (FWHM) of 20,000 or better and accuracy of about 20 ppm or less; such as a resolving power (FWHM) of 25,000 or better and accuracy of about 5 ppm or less; such as a resolving power (FWHM) of 25,000 or better and accuracy of about 3 ppm or less. Three exemplary mass spectrometers capable of exhibiting the requisite level of performance for IGF-I and/or IGF-II protein ions are those which include orbitrap mass analyzers, certain TOF mass analyzers, or Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring carbon containing molecules will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron≈1 amu). When molecular isotopic forms are ionized to multiply charged states, the mass distinction between the isotopic forms can become difficult to discern because mass spectrometric detection is based on the mass to charge ratio (m/z). For example, two isotopic forms differing in mass by 1 amu that are both ionized to a 5+ state will exhibit differences in their m/z of only 0.2 (difference of 1 amu/charge state of 5). High resolution/high accuracy mass spectrometers are capable of discerning between isotopic forms of highly multiply charged ions (such as ions with charges of ±5, ±6, ±7, ±8, ±9, or higher).

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z ratios and relative abundances for two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks or averaging the response from multiple peaks.

In mass spectrometric techniques generally, ions may be detected using several detection modes. For example, selected ions may be detected, i.e. using a selective ion monitoring mode (SIM), or alternatively, ions may be detected using a scanning mode. When operated in a scanning mode, the mass spectrometer typically provides the user with an ion scan; that is, the relative abundance of each ion with a particular mass/charge over a given range (e.g., 100 to 1000 amu). Further, when using instruments capable of multiple mass spectrometric events, such as certain ion trap or triple quadrupole instruments, mass transitions resulting from collision induced dissociation or neutral loss may be monitored, e.g., multiple reaction monitoring (MRM) or selected reaction monitoring (SRM).

The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, internal or external standards may be run with the samples, and a standard curve constructed based on ions generated from those standards. Using such a standard curve, the relative abundance of a given ion may be converted into an absolute amount of the original molecule. In certain preferred embodiments, one or more standards are used to generate a standard curve for calculating the quantity of an IGF-I and/or IGF-II protein. Methods of generating and using such standard curves are well known in the art and one of ordinary skill is capable of selecting an appropriate internal standard. For example, in preferred embodiments isotopically labeled or unlabeled intact non-human IGF-I and/or IGF-II (e.g., recombinant mouse IGF-I and/or IGF-II) or isotopically labeled intact human IGF-I and/or IGF-II may be used as a standard. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^{2}H$), $^{13}C$, and $^{15}N$. The isotopic label can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

In some embodiments, intact IGF-I and/or IGF-II in a sample are detected and/or quantified using MS as follows. The samples are subjected to liquid chromatography, preferably HPLC; the flow of liquid solvent from a chromatographic column enters a heated nebulizer interface of an ESI ionization source; and the solvent/analyte mixture is converted to vapor in the heated charged tubing of the interface. The analyte (e.g., intact IGF-I and/or IGF-II) contained in the solvent, is ionized by applying a large voltage to the solvent/analyte mixture. As the analyte exits the charged tubing of the interface, the solvent/analyte mixture nebulizes and the solvent evaporates, leaving analyte ions in various charge states. Quantitative data is then collected for the intensity of one or more of ions. The quantitative data for signal intensity for one or more ions is then collected and related to the quantity of intact IGF-I and/or IGF-II in the sample.

For intact IGF-I, ions in various charge states may be observed with m/z within the ranges of about 850.8±2 (9+), 957.1±2 (8+), 1093.7±2 (7+), and 1275.8±2 (6+). In some embodiments, data from one or more IGF-I ions with m/z within the range of about 1093.7±2 is collected and used for quantitation. Exemplary ions within this m/z range include IGF-I ions with m/z of about 1091.9±0.1, 1092.8±0.1, 1092.9±0.1, 1093.1±0.1, 1093.2±0.1, 1093.4±0.1, 1093.5±0.1, 1093.7±0.1, 1093.8±0.1, 1093.9±0.1, 1094.1±0.1, 1094.2±0.1, 1094.4±0.1, 1094.5±0.1, 1094.7±0.1, and 1095.4±0.1. This listing is not meant to be limiting. Numerous other ions may be suitable for use in the instant methods, as demonstrated in the spectrum shown in FIG. 3 (which demonstrates detection of groups of isotopic ions at m/z of about 828.0509±2, 850.7373±2, 871.8730±2, 920.5544±2, 939.6930±2, 956.9532±2, 975.4576±2, 1034.8128±2, 1051.6337±2, 1073.9335±2, 1093.6597±2, 1114.5219±2, 1207.9401±2, 1226.5705±2, 1252.5871±2, and 1275.6019±2; note, however, that as above, the ions of individual isotopes within these ranges will predominantly fall within the ranges of the indicated m/z±1. Also, at this level of precision, masses observed for any ion may vary slightly because of instrumental variance, e.g. ±0.1).

For intact IGF-II, ions various charge states may be observed with m/z within the ranges of about 934.69±2 (8+), 1068.07±2 (7+), 1245.92±2 (6+), and 1494.89±2 (5+). In some embodiments, data from one or more IGF-II ions with m/z within the range of about 1068.07±2 is collected and used for quantitation. Exemplary ions within this m/z range include IGF-II ions with m/z of about 1067.36±0.1, 1067.51±0.1, 1067.65±0.1, 1067.80±0.1, 1067.94±0.1, 1068.08±0.1, 1068.23±0.1, 1068.37±0.1, 1068.51±0.1, 1068.65±0.1, 1068.80±0.1, 1068.94±0.1, and 1069.08±0.1. In some embodiments, the one or more IGF-II ions are selected from the group consisting of IGF-II ions with m/z of about 1067.94±0.1 and 1068.08±0.1. This listing is not meant to be limiting and other ions may be suitable for use in the instant methods.

Figure 4:
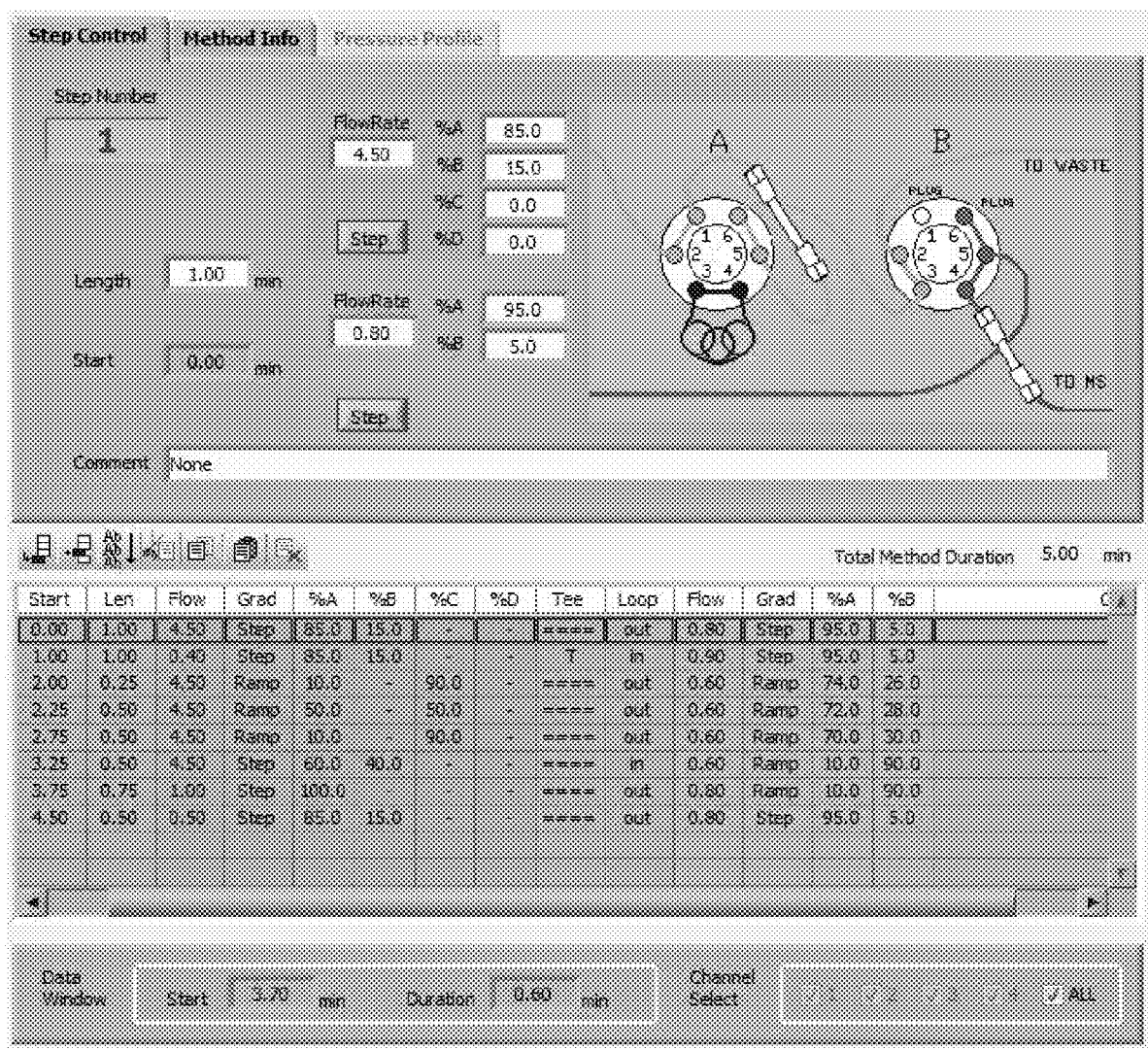
FIG. 4 shows LC gradient for Extraction and Analytical pumps. Mobile Phase A is Water with 0.1% Formic Acid and Mobile Phase B is 20% Isopropyl Alcohol, 80% Acetonitrile with 0.1% Formic Acid.

In some embodiments, the use of a high resolution/high accuracy mass spectrometer may allow for the signal intensity of a peak from a single isotopic form of a single ion (such as the single IGF-I ion peak shown in FIG. 4 at m/z of about 1093.66, or the single IGF-II peak shown in FIG. 12 at m/z of about 1067.80) to be selected for data acquisition. Alternatively, quantitative data for signal intensity from one or more isotopic forms of a single ion (such as one or more IGF-I or IGF-II isotopic forms as demonstrated in FIGS. 4 and 12), or signal intensity across a narrow m/z range (such as all IGF-I signal intensity for a m/z range of about 1093.7±1, or all IGF-II signal intensity for a m/z range of about 1068.2±1), may be collected and related to the quantity of intact IGF-I and/or IGF-II in the sample.

In some embodiments, quantitative data for signal intensity is collected for one or more IGF-I and/or IGF-II ions from at least two different charge states. The intensities of these ions may then be used for quantitative assessment of intact IGF-I and/or IGF-II in the sample. For example, IGF-I may be quantitated with signal intensity from one or more IGF-I ions at the 8+ charge state (i.e., IGF-I ions within a m/z range of about 957.1±2) and one or more IGF-I ions at the 7+ charge state (i.e., IGF-I ions within a m/z range 1093.7±2). In embodiments where quantitative data for signal intensity of two or more ions are collected, the intensities may be combined by any mathematical method known in the art (such as summation, or averaging the area under the curves) for quantitative assessment of intact IGF-I and/or IGF-II in the sample.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks are measured to determine the amount of an IGF-I and/or IGF-II protein or fragment. As described above, the relative abundance of a given ion may be converted into an absolute amount of the original analyte using calibration standard curves based on peaks of one or more ions of an internal molecular standard.

In some embodiments, IGF-I and IGF-II are quantitated simultaneously. In these embodiments, each IGF-I and IGF-II may each be quantitated by any of the methods provided above.

In certain preferred embodiments, the lower limit of quantitation (LLOQ) for IGF-I is within the range of about 15.0 ng/mL to 200 ng/dL, inclusive; preferably within the range of about 15.0 ng/dL to 100 ng/mL, inclusive; preferably within the range of about 15.0 ng/mL to 50 ng/mL, inclusive; preferably within the range of about 15.0 ng/mL to 25 ng/mL, inclusive; preferably within the range of about 15.0 ng/mL to 15 ng/mL, inclusive; preferably within the range of about 15.0 ng/mL to 10 ng/mL, inclusive; preferably about 15.0 ng/mL.

In certain preferred embodiments, the lower limits of quantitation (LLOQ) for IGF-II is within the range of about 30.0 ng/mL to 200 ng/dL, inclusive; preferably within the range of about 30.0 ng/dL to 100 ng/mL, inclusive; preferably within the range of about 30.0 ng/mL to 50 ng/mL, inclusive; preferably within the range of about 30.0 ng/mL to 25 ng/mL, inclusive; preferably within the range of about 30.0 ng/mL to 15 ng/mL, inclusive; preferably within the range of about 30.0 ng/mL to 10 ng/mL, inclusive; preferably about 30.0 ng/mL.

In certain preferred embodiments, the limit of detection (LOD) for IGF-I is within the range of about 4.9 ng/mL to 200 ng/mL, inclusive; preferably within the range of about 4.9 ng/mL to 100 ng/mL, inclusive; preferably within the range of about 4.9 ng/mL to 50 ng/mL, inclusive; preferably within the range of about 4.9 ng/mL to 25 ng/mL, inclusive;

preferably within the range of about 4.9 ng/mL to 20 ng/mL, inclusive; preferably about 4.9 ng/mL.

In certain preferred embodiments, the limits of detection (LOD) for IGF-II is within the range of about 8.2 ng/mL to 200 ng/mL, inclusive; preferably within the range of about 8.2 ng/mL to 100 ng/mL, inclusive; preferably within the range of about 8.2 ng/mL to 50 ng/mL, inclusive; preferably within the range of about 8.2 ng/mL to 25 ng/mL, inclusive; preferably within the range of about 8.2 ng/mL to 20 ng/mL, inclusive; preferably about 8.2 ng/mL.

The following Examples serve to illustrate the invention. These Examples are in no way intended to limit the scope of the methods. In particular, the following Examples demonstrate quantitation of IGF-I and IGF-II proteins or fragments by mass spectrometry with the use of a particular an internal standard. The use of the indicated internal standard is not meant to be limiting in any way. Any appropriate chemical species, easily determined by one in the art, may be used as an internal standard.

EXAMPLES

Example 1: Identification of IGF-1 Variants by Mass Spectrometry

Source of Specimens.

Specimens were originally submitted to Quest Diagnostics for quantitation of intact IGF-1 by LC-MS and were de-identified before further analysis. The IRB sponsor protocol number is BR13-002 and the IRB protocol number is 20121940.

Variant Database.

To find IGF-1 variants in patient specimens we used the Exome Aggregation Consortium database, ExAC (14) (accessed on Feb. 6, 2019, Supplemental Table 2), which contains all currently known variants including 13 of uncertain clinical significance: T4M, V17M, T29I, S34N, A38V, R55K, M59R, P66A, P66T, A67S, A67T, A70P, A70T; and the 3 previously reported pathogenic variants: V44M, R50W and R36Q.

Sample Preparation and LC-MS

Patient samples were prepared using modification of the methods previously described by Bystrom et al (3). Briefly, 100 µL aliquots of patient sera, quality controls (Bio-Rad), and calibrators (Ajinomoto) were thawed, vortexed, and transferred into a deep well plate (Thermo Scientific). A mixture of 10 µL of internal standard ($^{15}$N-labeled IGF-1, ProSpec) and 400 µL of acidified ethanol solution (87.5% EtOH, 12.5% 1 N HCl) was subsequently added and samples were vigorously mixed and incubated at room temperature for 30 min. Samples were then centrifuged (5,500 RCF for 10 minutes at 10° C.) and 350 µL of supernatant was mixed with 60 µL of 1.5 M Tris base. The samples were cooled for 60 min at −20° C. to generate additional protein precipitate, then centrifuged with previous settings.

After centrifugation, IGF-1 and its variants were extracted resolved using a multiplex high performance liquid chromatography (HPLC) system (Aria TLX-4) equipped with an on-line extraction (Thermo Scientific, San Jose, CA) using gradients (Supplemental FIG. 1) of water with 0.1% formic acid (mobile phase A) and acetonitrile with 0.1% formic acid (mobile phase B). The extraction column was a Phenomenex Monolithic Onyx C18 Guard Cartridge; the analytical column was a Phenomenex Kinetex C18 50×4.6 mm, 100 Å pore size. Mass spectrometry was performed with a Q Exactive Focus Hybrid Quadrupole-Orbitrap instrument (Thermo Scientific) equipped with heated electrospray ionization (HESI) source and operated in positive All Ion Fragmentation (AIF) mode, which has approximately double the sensitivity compared to a SIM scan mode (Supplemental FIG. 2 and Supplemental Table 1). The following MS parameters were used: Resolution 70,000; Scan range 1,060-1,110 Da; Normalized Collision Energy: 10; Automatic Gain Control (AGC): 2e4; Maximum Injection Time (IT): Auto. For the determination of the A67T/A70T pair, the mass-spectrometer was operating in Parallel Reaction Monitoring mode with resolution of 35,000, Isolation window 2.0 m/z, NCE 30, fixed first mass 150 Da, AGC: 2e4; MaxIT: 250 ms and 1 microscan.

MS Data Analysis and Visualization.

LC-MS data were analyzed by Thermo TraceFinder 5.0 Clinical and visualized with Qual Browser in Thermo Xcalibur v. 4.2.

DNA Sequencing Confirmation.

DNA extraction from de-identified serum specimen discards was performed with an Apostle MiniMax™ High Efficiency Isolation Kit (Beckman Coulter life science, Indianapolis, IN). Extracted DNA was used to sequence exon 4 region (Chr12:102419509-102419690 on Build GRCh38) and exon 3 region (Chr12:102475582-102475855 on Build GRCh38) of the IGF-1 gene. Primer design excluded common SNP positions (>1% population MAF). Sequencing was performed using the ABI Prism BigDye Terminator v3.1 cycle sequencing kit and the ABI 3500 genetic analyzer, according to the manufacturer's instructions (Applied Biosystems).

Results and Discussion

We have developed and automated the process of IGF-1 variants detection using concepts of Isotopic Peak Index (IPi) and relative Retention Time (rRT). Tandem mass-spectrometry is used to distinguish most common pair of variants A67T and A70T.

Isotopic Peak Index (IPi)

Based on the elemental composition of WT IGF-1 in its native non-reduced form ($C_{331}H_{513}N_{94}O_{101}S_7$) and its known variants, the peaks in the isotopic envelopes for each of the polypeptide's observed charge states can be precisely predicted in terms of their accurate m/z and the distribution of peak intensities.

In a previous work, we briefly described a nomenclature for peaks within the isotopic envelopes (12). Herein we further develop the concept of an "Isotopic Peak Index (IPi)" and an "Isotopic Peak relative Intensity (IPrI)" (FIG. 1). The isotopic envelopes of IGF-1 and variants, regardless of their monoisotopic m/z and charge state, follow this index-intensity distribution.

The IPi is a numerical index of a peak in an isotopic envelope, which is shown in the subscript and starts from zero. The monoisotopic peak is designated as $IP_0$ (reads "Isotopic Peak zero" or "IP zero"), and subsequent heavy isotopic peaks are identified as $IP_1$ through $IP_{13}$. This nomenclature applies to isotopic envelopes of the WT and all variants. For example, $IP_0$ of the V44M variant is designated as V44M0 and represents the monoisotopic peak in the isotopic envelope of the V44M variant. During routine detection and quantitation of WT IGF-1, the $IP_4$ is used under the label $WT_4$.

The IPrI is the distribution of intensities of peaks in an isotopic envelope. The specific pattern depends only on elemental composition of a molecule, which is very similar in IGF-1 variants, and thus the IPrI should be similar for WT and all variants. The distribution of the peak relative intensities in FIG. 1 is averaged from a real patient specimen and calculated relative to the intensity of the $IP_4$ peak as it is used for the quantitation of the WT IGF-1. The use of the relative intensity "qualifier" isotopes adjacent to the "quantifier" isotope to confirm IGF-1 identity is a practical example of using IPrI in the clinical field (7).

Monitoring all IGF-1 variants is challenging and has limitations. The mass resolution of the Orbitrap mass-analyzer in the Q Exactive Focus instrument (70,000 at m/z 200) is sufficient to recognize isotopic peaks within an isotopic envelope (0.14 m/z difference for $MH_7^{+7}$). A limitation of any MS approach is the inability to distinguish between isobaric variants A67T and A70T, as well as V17M and V44M. In addition, at present instrument resolution, variants with very close monoisotopic m/z (±10 ppm) cannot be resolved: R55K and R36Q; R50W, T4M and A67/70T. Lastly, the isotopic envelope of P66T variant overlaps with the WT IGF-1 and cannot be detected in routine analysis, since all P66T isotopic peaks have interference from the WT IGF-1 isotopic envelope.

Based on the theoretical isotopic envelopes for all variants, we identified peaks that cannot be resolved by calculating exact m/z shifts relative to the WT IGF based on differences in elemental composition of the variants as follows. The exact masses of monoisotopic peaks were first calculated for $MH_7^{+7}$ in all variants with non-reduced disulfide bonds (Supplemental Table 3). The table was then populated with exact m/z for the next 13 variant isotopes and re-grouped by sorting all the m/z values from lowest to highest (Isotopic Peak Master Table, Supplemental Table 4). Adjacent m/z differences of <10 ppm were identified and grouped as peaks that cannot be resolved one from another, but that can be resolved from peaks in other groups. In total, 5 m/z values (orange cells, Supplemental Table 4) were selected to monitor the WT and 4 variant groups (VG, Table 1).

Isotopic peaks of some variants belong to 2 variant groups (VG3 and VG4) with their IPrI providing additional confidence for their identification (Table 1). For example, the extracted ion chromatogram (EIC) of $S34N_2$ (VG3), is expected to be 57% of that of the $534N_4$ according to its relative intensity in the IGF-1 isotopic envelope (refer to FIG. 1). However, in the VG4, the $S34N_9$ is expected to be only 25% of WT, roughly half of the area of $S34N_2$. This difference in EICs can be used to distinguish S34N from other variants. By switching from VG4 to VG3 the sensitivity of the detection of S34N can be increased two-fold. The same applies to other variants from VG3, except A38V for which the sensitivity is higher in VG4.

Figure 2:
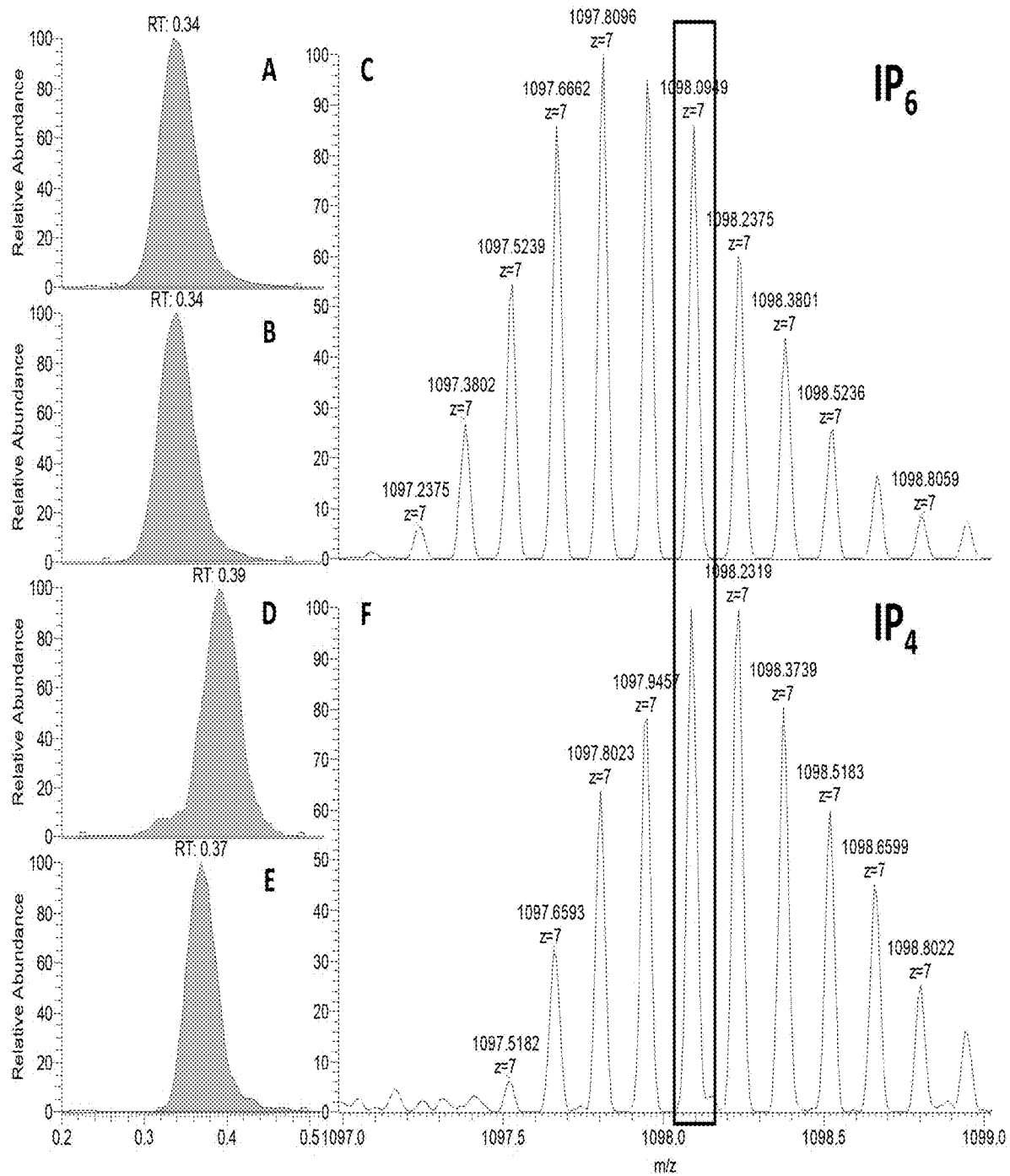
FIG. 2 shows LC-MS data containing a VG4 peak for specimens from two different patients. A EIC of $WT_4$ for Patient 1; B EIC of VG4 for Patient 1; C Variant isotopic envelope for Patient 1, rectangle indicates that $IP_6$ was detected at VG4; D EIC of $WT_4$ for Patient 2; E EIC of VG4 for Patient 2; F Variant isotopic envelope for Patient 2, rectangle indicates that $IP_4$ was detected at VG4.

In our method, all variants are monitored with only 4 m/z ratios (Table 1). The presence of a peak at any of these m/z ratios will indicate that a variant belonging to a given VG is present. For example, FIG. 2 shows LC-MS data containing a VG4 peak for specimens from two different patients. Because $IP_6$ was detected as VG4 m/z in the specimen from patient 1, the $IP_i$ concept predicts (Table 1) that patient 1 must have a R50W, T4M, A67T, or A70T variant. Similarly, because $IP_4$ was detected as VG4 m/z in the specimen from patient 2, it should have either V17M or V44M variant. DNA sequencing confirmed that patient 1 had A70T and patient 2 had V44M, thus providing validation of IPi as an approach for distinguishing variants. Most variants can be distinguished using the IPi approach alone, i.e. based only on the isotopic distribution of peaks in their mass spectra.

Although the approach is targeted, it can also result in discovery of new variants. Close examination of LC-MS data from a patient specimen from which a member of VG2 was detected revealed that the IPi matched neither of the 2 variants in VG2: A67S ($IP_4$) nor T29I ($IP_8$). Instead, the peak corresponded to either an $IP_{10}$ or $IP_{11}$ (Supplemental FIG. 3). DNA sequencing revealed a variant S33P, consistent with the calculated m/z 1095.8130 for 533P10, (6 ppm different from the VG2 m/z, Supplemental Table 4), but not the ExAC database, thus validating IPi as an approach for discovery of new variants.

Relative Retention Time (rRT)

Our preliminary studies show that some IGF-1 variants do not coelute with the WT. This difference between RT of the WT and that of a variant is designated as Relative Retention Time (rRT) and it can be used to distinguish between variants. By using the IPi concept to predict and assign variants to the different VGs, comparing their observed rRTs, and confirming their identity by DNA-sequencing, we validated rRT as a tool for variant differentiation and discovery (Table 2).

For example, the EICs of the $WT_4$ and VG4 indicate slight differences in rRTs for known IGF-1 variants from 2 specimens, thus differentiating variant A70T (FIG. 2B), which co-elutes with the WT (FIG. 2A), from V44M (FIG. 2E), which elutes later than the WT (FIG. 2D).

Notably, in some VGs the IPi predicted a single variant yet the rRT revealed the presence of new IGF-1 variants (Table 2). For example, there is only one known variant that can have an $IP_1$ at the VG3 m/z (A38V), which should coelute with the WT. However, we found specimens in which an $IP_1$ variant eluted slightly later that the WT. DNA sequencing confirmed that coeluting variant was the A38V, whereas the later eluting variant was A67V, a variant not in the ExAC database, i.e., a variant which has the same amino acid substitution, but at a different position (Table 2) Similarly, for $IP_4$ in VG1 we found in a patient specimen an unreported Y31H variant, with only a 1.5 ppm difference in calculated m/z compared to P66A (Supplemental Table 2) and eluting slightly earlier than the WT (Table 2). Also in VG1, the rRT indicated the presence of new variants R50Q or R56K, which were identified by DNA sequencing. Both of these new variants had the identical amino acid substitutions as known variants but at different positions (Table 2). These examples provide validation of rRT being a tool for variant identification and discovery of new variants.

Tandem Mass-Spectrometry

In the ExAC database, the frequency of occurrence of A67T and A70T is the highest (93% combined, Supplemental Table 1, constructed from ExAC browser). They can be distinguished from each other by differences in the m/z for $y_3$ fragment ion, and from the WT by differences in the m/z for the $y_5$ fragment ion (Supplemental Table 5), upon reanalysis by MS/MS. In our workflow, we employ Parallel Reaction Monitoring (PRM) with an inclusion list: m/z 1093.5215 ($WT_4$) and 1098.0969 ($VG4$).

We validated this approach using specimens in which $IP_6$ of VG4 was detected indicating presence of A67T, A70T, T4M or R50W variants. For example, upon reanalysis of two patient specimens, MS/MS spectra revealed y ions confirming that the patient were heterozygous for WT and A67T (patient A), and A70T (patient B) variants, respectively (Supplemental FIG. 4). In total, we confirmed that MS/MS matched DNA sequencing results in 28 tested specimens: 9 with A67T and 19 with A70T variants.

Figure 5:
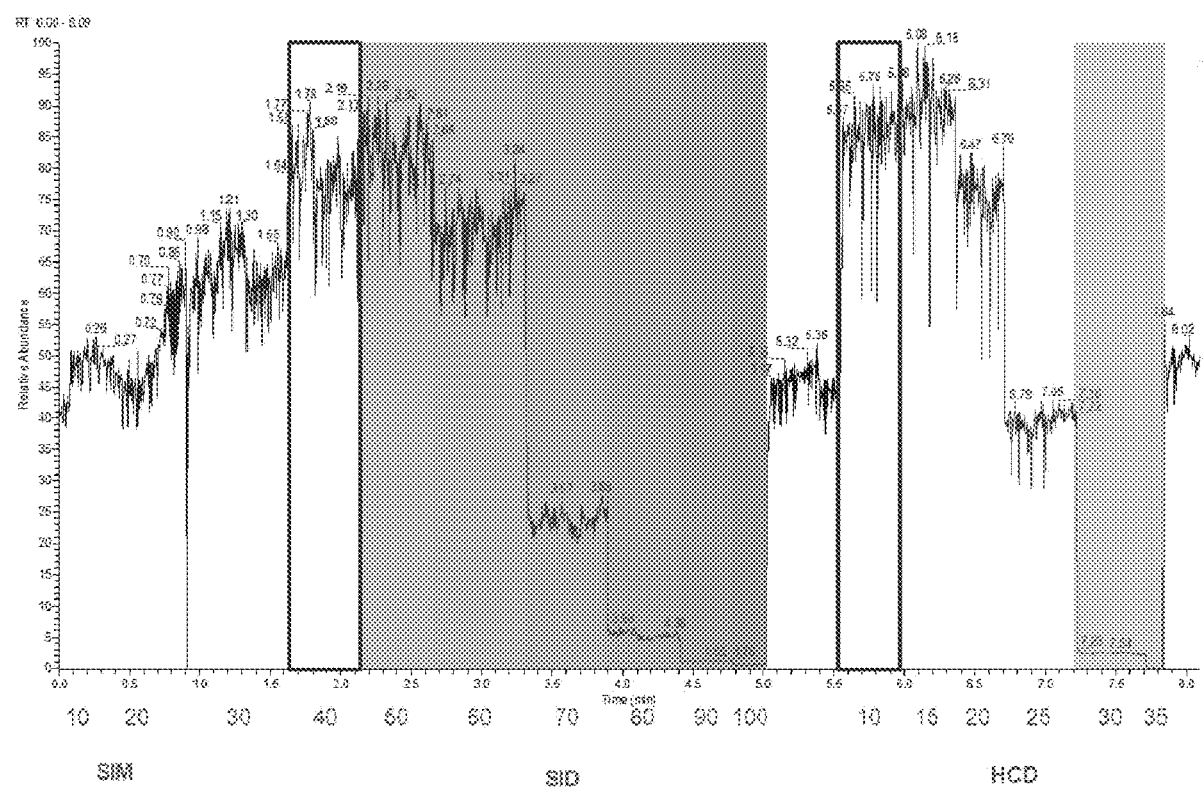
FIG. 5 shows comparison of SIM scan with in-source CID (SID) and HCD of various energies. Red rectangles outline highest sensitivity.
Figure 6:
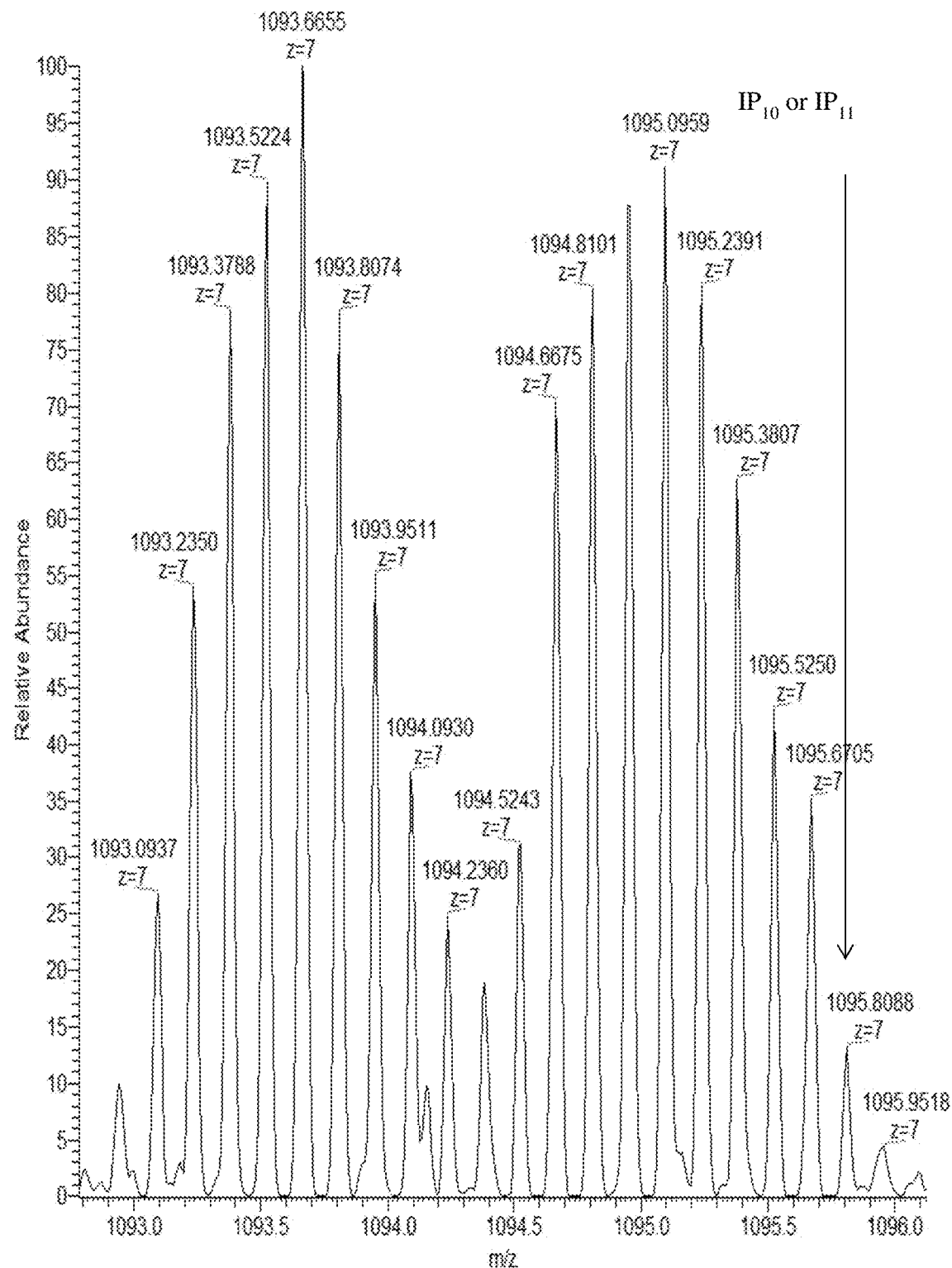
FIG. 6 shows an unknown variant from VG2. The peak at VG2 m/z corresponded to either an $IP_{10}$ or $IP_{11}$, which didn't match any known variants from that group (either $IP_4$ or $IP_8$). DNA sequencing reveal a variant S33P, consistent with the calculated m/z 1095.8130 for 533P10, (6 ppm different from the VG2 m/z).
Figure 7:
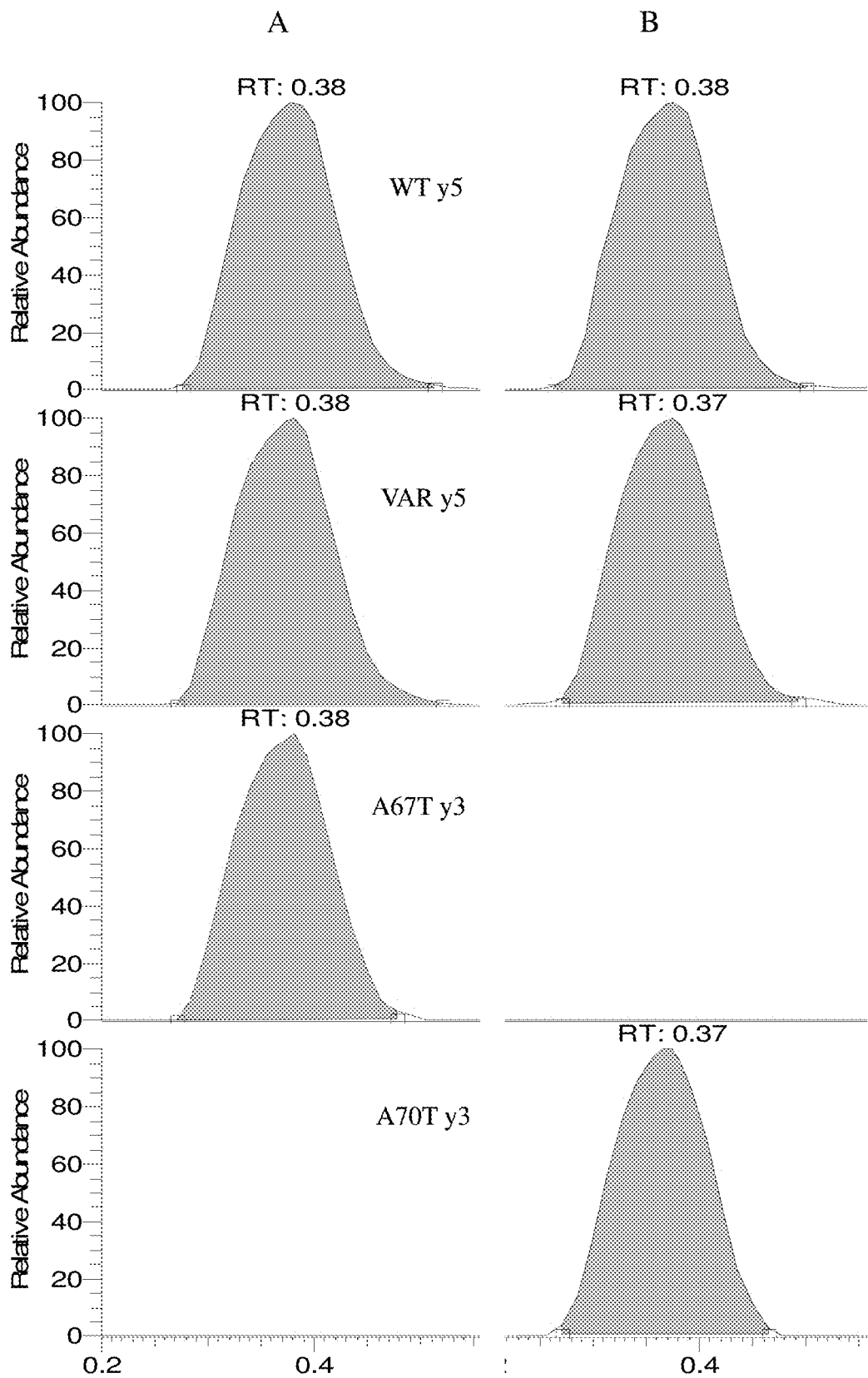
FIG. 7 shows extracted ion chromatograms for selected y-ions after tandem MS/MS indicating presence of WT and variant A67T in patient specimen A and WT and variant A70T in patient specimen B.
Figure 8:
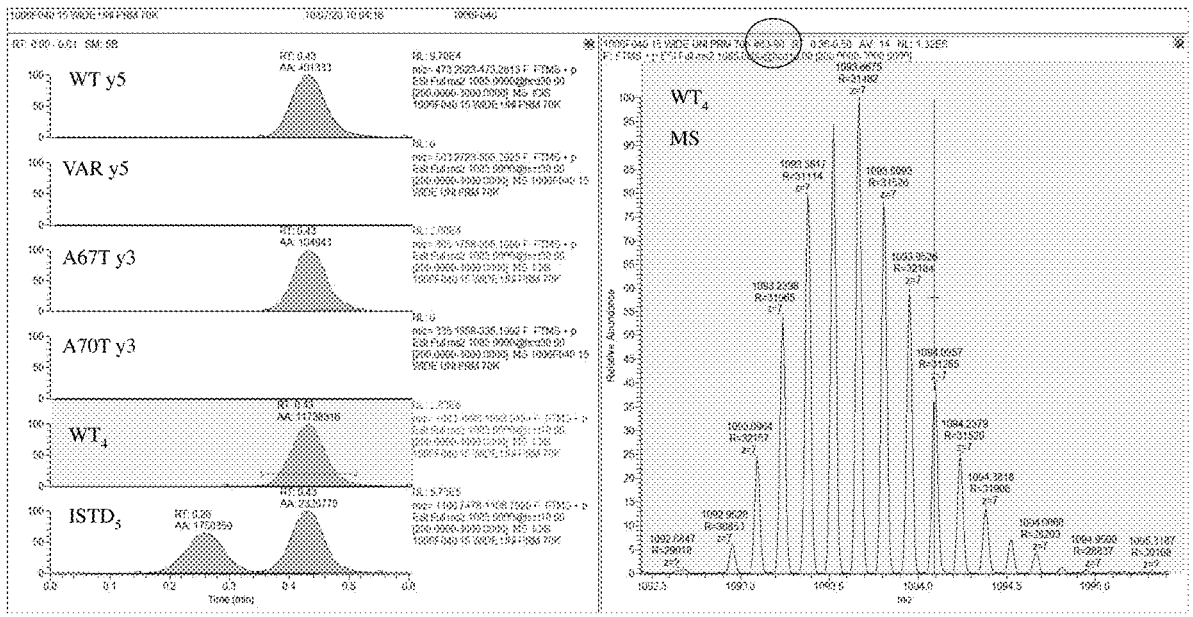
FIG. 8 shows simultaneous IGF-1 quantitation and detection of IGF-1 variants. The MS experiment is designed as a two cycling wide-isolation-window PRM scans with low (10) and high (30) NCE. The low energy scan can be used to detect and quantify IGF-1, while high energy scan can be used to extract y ions that a reused to distinguish between A67T and A70T variants. The number of scans per quantitative peak is in this case 13, which can be further increased with a faster instrument or lower detector resolution.
Figure 9:
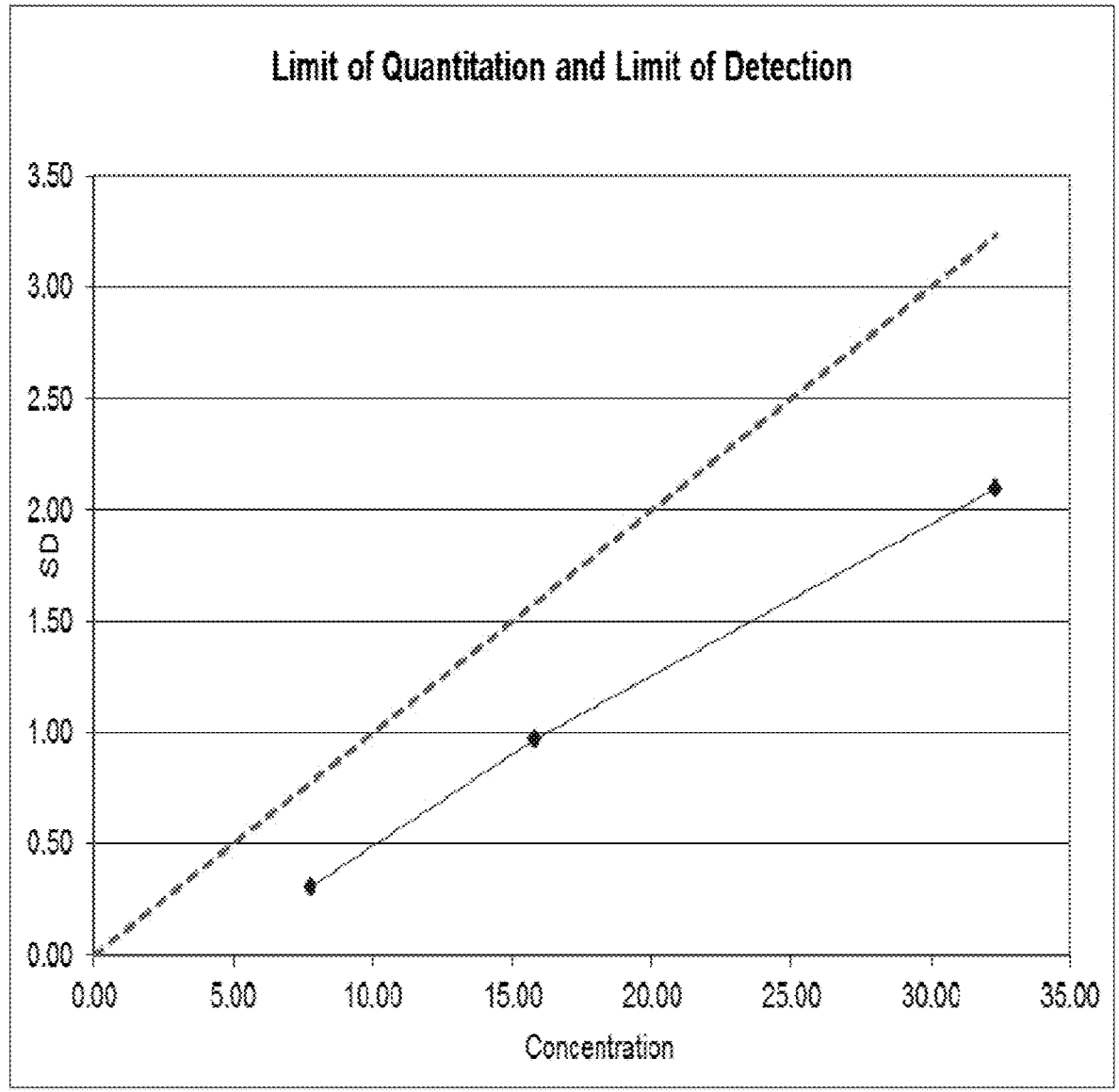
FIG. 9 shows IGF-1 assay Limit of Quantitation and Limit of Detection. The values of concentration (x-axis) and SD (y-axis) are in ng/mL.
Figure 10:
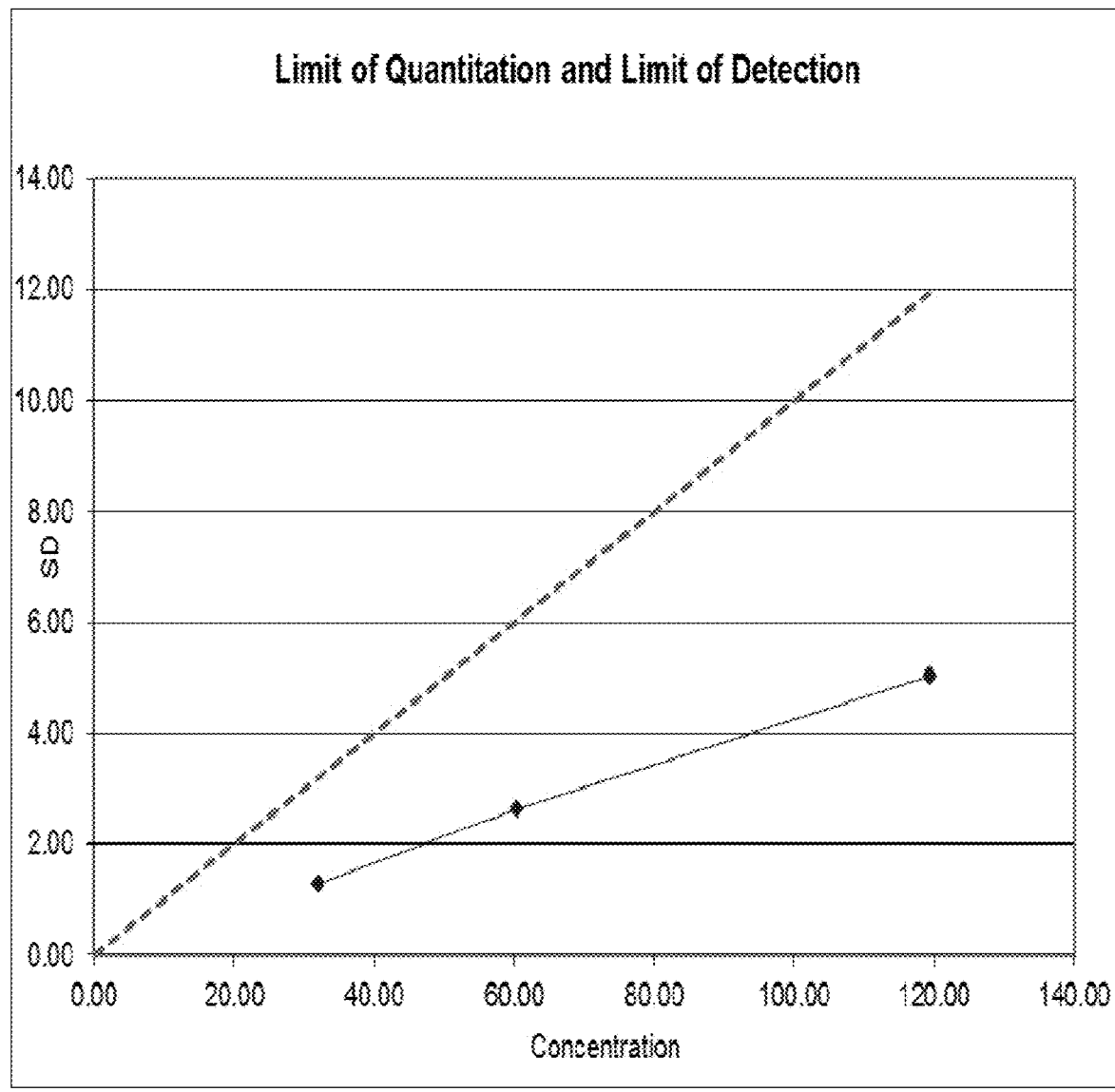
FIG. 10 shows IGF-2 assay Limit of Quantitation and Limit of Detection. The values of concentration (x-axis) and SD (y-axis) are in ng/mL.
Figure 11:
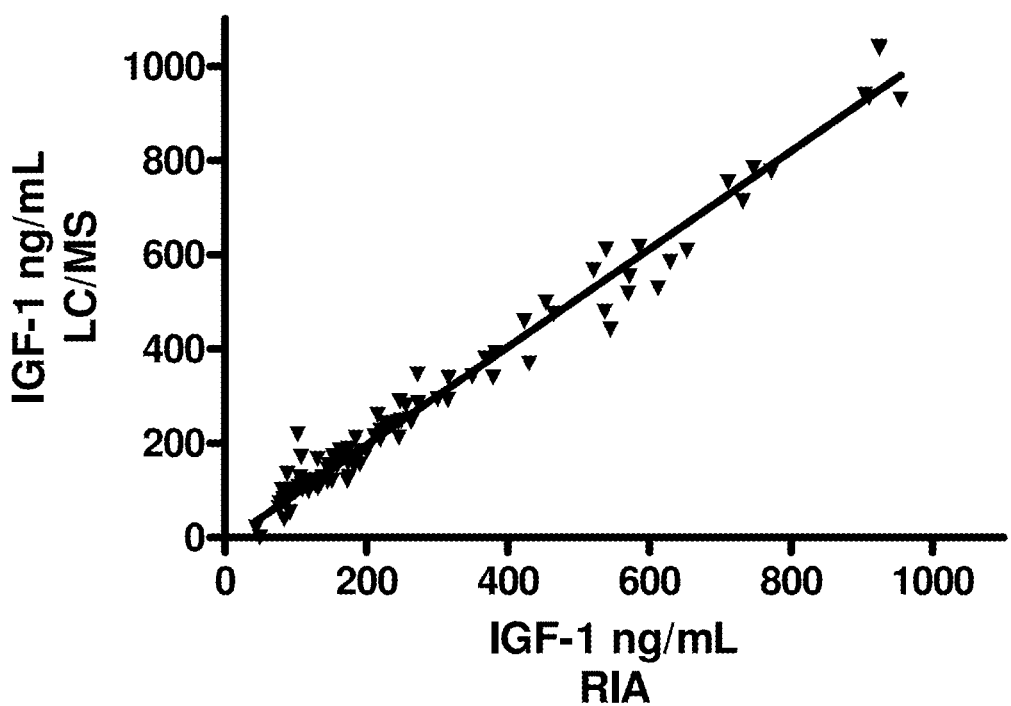
FIG. 11 shows IGF-1assay split sample comparison of LC-MS vs RIA.

While the potential exists for detecting A67T and A70T in a single run by employing alternating MS and MS/MS scans (Supplemental FIG. 5), this workflow would have to be proven not to compromise IGF-1 quantitation due to having fewer MS scans across a chromatographic peak. Further, the workflow may be hard to justify given that the most abundant polymorphisms A67/70T are present in only 0.2% of patient specimens (Supplemental Table 2).

Automated Variant Detection

IGF-1 variant detection was automated and incorporated to the routine IGF-1 quantitation workflow. All spectra were analyzed with Thermo TraceFinder 5.0 Clinical with mass extraction tolerance set to 20 ppm. The TraceFinder Master method was set up to search specimen spectra for the following compounds: $WT_4$ (plus $WT_3$ and $WT_5$ as qualifiers), Internal Standard (ISTDs) and the m/z corresponding to four Variant Groups, which were designated as Internal Standards. The software produced two reports.

For Variant Report, TraceFinder Report Type was set up as Batch with the following Filter string:

AND(quanresults.sampleType="Specimen", quanresults.totalArea< >"N/F", quanresults.peakArea>300000, compound.compoundname< >"IGF-1", Compound.CompoundName< >"ISTD")

This generates a list (FIG. 3, panel A) of specimen that are suspected to contain an IGF-1 variant. In the example shown, the specimen is suspected to contain a VG4 variant. The information about the presence of the variant is then reported to a physician via a standard comment in the Laboratory Information System (LIS)

Based on the mass-spectrometric data, a rare heterozygous IGF-1 variant was detected in this specimen. The level of this variant was not included in the reported IGF-1 result above, which explains a potentially lower than expected value. The level of the variant is expected to be the same as the value reported for the Wild Type IGF-1 protein. The clinical significance of this IGF-1 variant remains unknown. Additional DNA sequencing is recommended to confirm the presence of the variant.

Using IPi and rRT concepts, the identity of the variant can be predicted and then confirmed with DNA sequencing or tandem mass-spectrometry in case of A67T/A70T pair.

Figure 3:
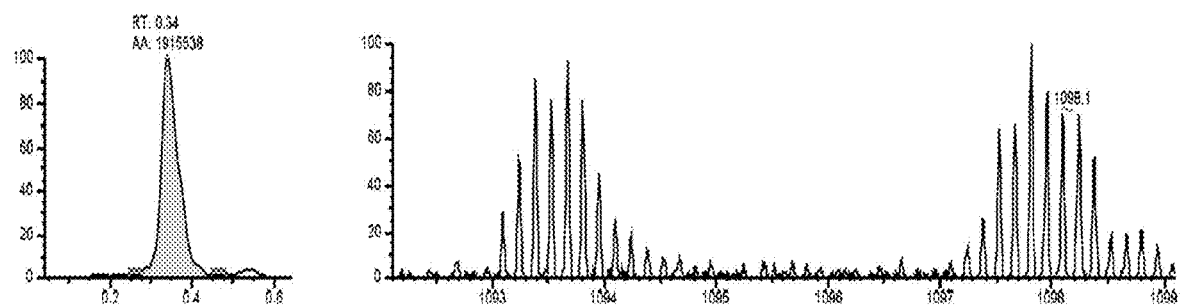
FIG. 3 shows automated IGF-1 variant detection. Reports are generated with TraceFinder 5.0 Clinical. The Variant Report displays only specimen suspected to contain IGF-1 variants. IGF-1 Quantitation Report marks suspected homozygous variants.
Figure 3:
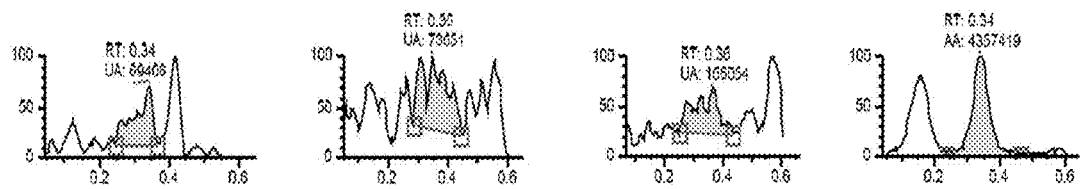

The IGF-1 Quantitation Report is designed to show the information relevant to the WT detection and quantitation (FIG. 3, panel B). The TraceFinder Report Type is set up as Compound custom formula <compound. compound Type="eTargetCompound">. In addition to this, the report uses the following cell formula IF(AND(sample.sampletype="Specimen", quanresults.peaksfound=FALSE), "POSSIBLE HOMO VAR", IF(AND(sample.sampletype="Specimen", quanresults. peaksfound=TRUE), IF(quanresults.calcamount-compoundloq<0, "POSSIBLE HOMO VAR", " "), " "))

to label specimens that are suspected to contain a homozygous IGF-1 variant. In this case, the results are manually inspected, the level of the variants is estimated based on the WT IGF-1 calibration curve and reported to a physician via a standard comment in the LIS system (quantitative value is used as an example)

Based on the mass-spectrometric data, a rare homozygous IGF-1 variant was detected in this specimen. The level of the variant was not included in the reported IGF-1 result above. This explains the reported IGF-1 concentration, as all IGF-1 is produced in the form of the variant protein. Estimated concentration of the variant is 75 ng/mL. The clinical significance of this variant remains unknown. Additional DNA sequencing is recommended to confirm the presence of the variant.

Clinical Applications

We have developed a robust high throughput detection and discovery of IGF-1 variants using high resolution LC-MS methods in a clinical laboratory. Individual methods, $IP_i$, rRT and MS/MS, for distinguishing and discovering variants were validated by the DNA sequencing. Our approach of simultaneous monitoring and identifying IGF-1 variants is a significant improvement compared to other methods in clinical laboratories. The automated interpretation of LC-MS data by commercially available instrument software reduces risk for human error.

During development and validation of our approach, we identified 6 variants from the ExAC database: P66A, A67S, S34N, A38V, A67T, A70T, and 2 previously reported V44M and A67V variants. In addition, the approach discovered 6 previously unreported variants Y31H, S33P, R50Q, R56K, T41I, and A62T. Considering high number of new discoveries, it becomes evident that the current knowledge of IGF-1 variants is limited and the world of IGF-1 variants is more vast.

We anticipate that our methodology may be more generally applied to high resolution LC-MS approaches for automated quantitation of polypeptides and proteins and efficient detection of their polymorphic variants in clinical laboratories. For IGF-1, the methods provide an opportunity to provide clinicians more profile of a patient's IGF-1 status, as well as an opportunity to further explore genotype-phenotype relationships.

In future, the list of the monitored IGF-1 variants will include any newly reported ones. It is also possible to develop an MS/MS strategy for DNA sequencing-free confirmation of P66T, A67S, and A67V variants. Considering current improvements in mass-spectrometers and their scan speeds, parallel MS quantitation of the WT IGF-1 and MS/MS verification of some of its variants may become possible in clinical laboratories.

By applying this approach to data from a large number of specimens, in future work we aim to compare the frequency of occurrence of different IGF-1 variants between general and clinical populations. Discrepancies in the frequencies of occurrence may implicate variants as being pathogenic or likely pathogenic—thus informing diagnosis and patient care.

TABLE 1

WT and Variant Groups are monitored at 5 m/z ratios. In the Table, IGF-1 variants are shown with their respective Isotopic Peak Indices.

| Group | m/z | Variant Peaks Covered |
|---|---|---|
| WT | 1093.52149 | $WT_4$, $P66T_1$ |
| VG1 | 1089.80497 | $P66A_4$, $R55K_6$, $R36Q_6$ |
| VG2 | 1095.80648 | $A67S_4$, $T29I_8$ |
| VG3 | 1097.09596 | $S34N_2$, $A70P_3$, $A38V_1$, $M59R_4$, $A67S_{13}$ |
| VG4 | 1098.09687 | $S34N_9$, $A70P_{10}$, $A38V_8$, $M59R_{11}$, $V17/44M_4$, $R50W_6$, $T4M_6$, $A67/70T_6$ |

TABLE 2

Relative retention time comparison of variants after IPi prediction.

| Group | $IP_i$ | IPi predicted variant | rRT, min | DNA confirmed variant |
|---|---|---|---|---|
| VG1 | $IP_6$ | R36Q | −0.01 | R50Q |
|  |  | R55K | +0.12 | R56K |
|  | $IP_4$ | P66A | +0.02 | P66A |
|  |  |  | −0.07 | Y31H |

TABLE 2-continued

Relative retention time comparison of variants after IPi prediction.

| Group | IP$_i$ | IPi predicted variant | rRT, min | DNA confirmed variant |
|---|---|---|---|---|
| VG2 | IP$_8$ | T29I | +0.02 | T41I |
|  | IP$_4$ | A67S | −0.01 | A67S |
|  | IP$_{10}$ | UNKN | 0.00 | S33P |
| VG3 | IP$_2$ | S34N | −0.01 | S34N |
|  | IP$_1$ | A38V | 0.00 | A38V |
|  |  |  | +0.04 | A67V |
| VG4 | IP$_6$ | R50W | 0.00 | A67T |
|  |  | T4M |  | A70T |
|  |  | A67T |  |  |
|  | IP$_4$ | A70T | +0.04 | A62T |
|  |  | V17M | −0.02 | V44M |
|  |  | V44M |  |  |

Within each Variant Group, the IPi concept was applied for each variant detected. After IPi prediction the rRT was identified and compared within unresolved variants. rRT led to separation of R50Q from R56K variants, as well as A38V from A67V. It also resulted in discovery of Y31H, S33P and A62T variants.

TABLE 3

The summary of Comparison of SIM scan with in source CID (SID) and HCD of various energies as shown in calibrators and QCs. Results indicate significant increase in response for first calibrators and Internal Standard (yellow highlighted cell) with application of

| SIM | Area | Calculated Amt | % Diff | ISTD Response |  | Area | Calculated Amt | % Diff | ISTD Response |  |
|---|---|---|---|---|---|---|---|---|---|---|
| Blank_001 | 101380 | 14.649 | N/A | 7261043 |  | 116316 | 13.996 | N/A | 6654901 |  |
| IGF-I_Cal_1 | 119822 | 18.008 | 15.43 | 6389304 |  | 140829 | 15.509 | −0.58 | 7157109 |  |
| IGF-I_Cal_2 | 230708 | 29.825 | −4.71 | 6477114 |  | 245616 | 27.477 | −12.22 | 6628045 |  |
| IGF-I_Cal_3 | 491149 | 56.014 | −10.38 | 6724915 |  | 587753 | 63.922 | 2.27 | 6531497 |  |
| IGF-I_Cal_4 | 1077342 | 122.588 | −1.93 | 6397715 |  | 1172879 | 122.968 | −1.63 | 6673875 |  |
| IGF-I_Cal_5 | 2260980 | 248.536 | −0.59 | 6464017 |  | 2445003 | 264.191 | 5.68 | 6419952 |  |
| IGF-I_Cal 6 | 4369568 | 511.028 | 2.21 | 5970112 |  | 5395022 | 526.009 | 5.2 | 7088551 |  |
| IGF-I_Cal_7 | 9491725 | 1000.827 | 0.08 | 6502264 |  | 10446948 | 1061.041 | 6.1 | 6791975 |  |
| IGF-I_Cal_8 | 19311796 | 1997.549 | −0.12 | 6436243 |  | 21978727 | 1903.283 | −4.84 | 7959438 |  |
| Blank_002 | 56920 | 10.931 | N/A | 6573854 |  | 67553 | 10.436 | N/A | 5488401 |  |
| IGF-I_LowQC | 386060 | 53.8 | 25.12 | 5525483 |  | 364282 | 43.364 | 0.85 | 6058154 |  |
| IGF-I_MediumQC | 1277222 | 162.845 | 1.91 | 5645623 |  | 1391095 | 159.169 | −0.39 | 6092802 |  |
| IGF-I_HighQC | 2495724 | 350.954 | 12.09 | 5009301 |  | 2604007 | 336.041 | 7.33 | 5366939 |  |
| IGF-I_InHouseQC | 649180 | 79.035 | 15.38 | 6126141 | 6250224 | 706561 | 73.928 | 7.92 | 6760096 | 6547981 |

| SID40 | Area | Calculated Amt | % Diff | ISTD Response |  | Area | Calculated Amt | % Diff | ISTD Response |  |
|---|---|---|---|---|---|---|---|---|---|---|
| Blank_001 | 27191 | 1.276 | N/A | 11354131 |  | 52513 | 7.323 | N/A | 8948204 |  |
| IGF-I_Cal_1 | 215562 | 16.216 | 3.95 | 9373546 |  | 203573 | 17.616 | 12.93 | 9511498 |  |
| IGF-I_Cal_2 | 532439 | 30.737 | −1.8 | 12370617 |  | 355645 | 28.775 | −8.07 | 9299471 |  |
| IGF-I_Cal_3 | 938706 | 64.093 | 2.55 | 10528753 |  | 850021 | 64.413 | 3.06 | 9236839 |  |
| IGF-I_Cal_4 | 2094107 | 120.586 | −3.53 | 12503214 |  | 1476250 | 112.218 | −10.23 | 8992197 |  |
| IGF-I_Cal_5 | 3442142 | 243.338 | −2.66 | 10163724 |  | 3087340 | 247.479 | −1.01 | 8382691 |  |
| IGF-I_Cal_6 | 6383731 | 502.987 | 0.6 | 9052145 |  | 6617528 | 496.069 | −0.79 | 8901024 |  |
| IGF-I_Cal_7 | 14990955 | 1011.591 | 1.16 | 10405111 |  | 12480885 | 1064.183 | 6.42 | 7796540 |  |
| IGF-I_Cal_8 | 22520511 | 1994.807 | −0.26 | 7690509 |  | 25448075 | 1953.647 | −2.32 | 8646531 |  |
| Blank_002 | 81391 | 4.932 | N/A | 10948617 |  | 92880 | 10.662 | N/A | 8515330 |  |
| IGF-I_LowQC | 496726 | 53.112 | 23.52 | 6715770 |  | 448360 | 42.268 | −1.7 | 7650411 |  |
| IGF-I_MediumQC | 1759620 | 150.007 | −6.13 | 8443815 |  | 2164910 | 158.749 | −0.66 | 9236236 |  |
| IGF-I_HighQC | 2900310 | 311.435 | −0.53 | 6679379 |  | 3472426 | 282.721 | −9.7 | 8238577 |  |
| IGF-I_InHouseQC | 676037 | 63.616 | −7.13 | 7639159 | 9562035 | 721472 | 64.948 | −5.19 | 7771706 | 8651947 |

| HCD10 | Area | Calculated Amt | % Diff | ISTD Response |  | Area | Calculated Amt | % Diff | ISTD Response |  |
|---|---|---|---|---|---|---|---|---|---|---|
| Blank_001 | 158701 | 9.284 | N/A | 12427410 |  | 122008 | 6.268 | N/A | 12354060 |  |
| IGF-I_Cal_1 | 474108 | 18.956 | 21.51 | 11866750 |  | 529487 | 17.612 | 12.9 | 12995929 |  |
| IGF-I_Cal_2 | 1150015 | 26.822 | −14.31 | 18537079 |  | 992599 | 29.235 | −6.6 | 13716006 |  |
| IGF-I_Cal_3 | 2539204 | 59.725 | −4.44 | 16464145 |  | 1990611 | 58.039 | −7.14 | 13205065 |  |
| IGF-I_Cal_4 | 5937240 | 127.636 | 2.11 | 17285566 |  | 4024978 | 124.229 | −0.62 | 12165565 |  |
| IGF-I_Cal_5 | 10032157 | 229.563 | −8.17 | 16052573 |  | 9234525 | 255.922 | 2.37 | 13399121 |  |
| IGF-I_Cal_6 | 25231298 | 502.21 | 0.44 | 18515446 |  | 16582517 | 491.01 | −1.8 | 12478676 |  |
| IGF-I_Cal_7 | 39464040 | 1038.468 | 3.85 | 14353983 |  | 33291685 | 1009.297 | 0.93 | 12154060 |  |
| IGF-I_Cal_8 | 81037160 | 1980.719 | −0.96 | 16276420 |  | 67383599 | 1999.056 | −0.05 | 12404253 |  |
| Blank_002 | 327319 | 13.133 | N/A | 13875385 |  | 169692 | 7.744 | N/A | 12216508 |  |
| IGF-I_LowQC | 1378221 | 46.03 | 7.05 | 11891938 |  | 1318658 | 41.901 | −2.56 | 12343310 |  |
| IGF-I_MediumQC | 3681530 | 144.054 | −9.85 | 9463407 |  | 5027791 | 153.531 | −3.92 | 12245524 |  |
| IGF-I_HighQC | 6780438 | 281.692 | −10.03 | 8831907 |  | 8948900 | 302.251 | −3.47 | 10976871 |  |
| IGF-I_InHouseQC | 1978500 | 65.351 | −4.6 | 11641143 | 14105939 | 2364701 | 71.966 | 5.06 | 12535459 | 12513601 |

HCD of 10 NCE.

TABLE 4

List of IGF-1 variants from ExAC database

| Source | Variant | Allele Count | Total Alleles | Allele Frequency, % × 1000 |
|---|---|---|---|---|
| ExAC DB | T 4 M | 1 | 121,092 | 0.083% |
|  | V 17 M | 2 | 120,976 | 0.165% |
|  | T 29 I | 1 | 120,640 | 0.083% |
|  | S 34 N | 1 | 120,892 | 0.083% |
|  | A 38 V | 2 | 121,000 | 0.165% |
|  | R 55 K | 2 | 121,210 | 0.165% |
|  | M 59 R | 1 | 121,188 | 0.083% |
|  | P 66 A | 9 | 121,134 | 0.743% |
|  | P 66 T | 1 | 121,134 | 0.083% |
|  | A 67 S | 1 | 121,138 | 0.083% |
|  | A 67 T | 158 | 121,138 | 13.043% |
|  | A 70 P | 1 | 121,116 | 0.083% |
|  | A 70 T | 74 | 121,116 | 6.110% |

Theoretical accurate m/z of all IGF-1 variants and their isotopic peaks at a charge state +7 and non-reduced disulfide bonds.

TABLE 6

Isotopic Peaks Master Table.
Isotopic Peaks Master Table

| $IP_i$ | m/z | ppm |
|---|---|---|
| $R36Q_0$ | 1088.9421 |  |
| $R55K_0$ | 1088.9473 | 4.8 |
| $R36Q_1$ | 1089.0854 | 126.8 |
| $R55K_1$ | 1089.0906 | 4.8 |
| $R36Q_2$ | 1089.2287 | 126.8 |
| $P66A_0$ | 1089.2316 | 2.6 |
| $R55K_2$ | 1089.2339 | 2.1 |
| $R36Q_3$ | 1089.3721 | 126.8 |
| $P66A_1$ | 1089.3750 | 2.6 |
| $R55K_3$ | 1089.3773 | 2.1 |

TABLE 5

Variant isotopic peak's m/z

| Variant | Elemental change | Δ m/z | Isotopic Peak Index | | | | | | |
|---|---|---|---|---|---|---|---|---|---|
|  |  |  | 0 | 1 | 2 | 3 | 4 | 5 | 6 |
| R36Q | +O—CH4N2 | −4.0061 | 1088.9421 | 1089.0854 | 1089.2287 | 1089.3721 | 1089.5154 | 1089.6588 | 1089.8021 |
| R55K | —N2 | −4.0009 | 1088.9473 | 1089.0906 | 1089.2339 | 1089.3773 | 1089.5206 | 1089.6640 | 1089.8079 |
| P66A | —C2H2 | −3.7165 | 1089.2316 | 1089.3750 | 1089.5183 | 1089.6616 | 1089.8050 | 1089.9483 | 1090.0916 |
| IGF-1 |  | 0.0000 | 1092.9482 | 1093.0915 | 1093.2348 | 1093.3782 | 1093.5215 | 1093.6648 | 1093.8082 |
| P66T | +O—C | 0.5707 | 1093.5189 | 1093.6622 | 1093.8055 | 1093.9489 | 1094.0922 | 1094.2355 | 1094.3789 |
| T29I | +C2H4—O | 1.7195 | 1094.6676 | 1094.8110 | 1094.9543 | 1095.0976 | 1095.2410 | 1095.3843 | 1095.5276 |
| A67S | +O | 2.2850 | 1095.2331 | 1095.3765 | 1095.5198 | 1095.6631 | 1095.8065 | 1095.9498 | 1096.0932 |
| M59R | +CH3N3—S | 3.5801 | 1096.5282 | 1096.6716 | 1096.8149 | 1096.9582 | 1097.1016 | 1097.2449 | 1097.3883 |
| A70P | +C2H2 | 3.7165 | 1096.6647 | 1096.8080 | 1096.9513 | 1097.0947 | 1097.2380 | 1097.3813 | 1097.5247 |
| S34N | +CHN | 3.8587 | 1096.8069 | 1096.9502 | 1097.0935 | 1097.2369 | 1097.3802 | 1097.5235 | 1097.6669 |
| A38V | +C2H4 | 4.0045 | 1096.9526 | 1097.0960 | 1097.2393 | 1097.3826 | 1097.5260 | 1097.6693 | 1097.8126 |
| r50w | +C5—H2—N2 | 4.2826 | 1097.2308 | 1097.3741 | 1097.5174 | 1097.6608 | 1097.8041 | 1097.9474 | 1098.0908 |
| T4M | +CH2—O | 4.2847 | 1097.2328 | 1097.3762 | 1097.5195 | 1097.6628 | 1097.6082 | 1097.9495 | 1098.0929 |
| A67/70T | +CH2O | 4.2872 | 1907.2354 | 1097.3787 | 1097.5220 | 1097.6654 | 1097.8087 | 1097.9520 | 1098.0954 |
| V17/44M | +S | 4.5674 | 1097.5156 | 1097.6589 | 1097.8023 | 1097.9456 | 1098.0889 | 1098.2323 | 1098.3756 |
| Y31H | —C3—H2 + N2—O | −3.7149 | 1089.2332 | 1089.3766 | 1089.5199 | 1089.6632 | 1089.8066 | 1089.9499 | 1090.0932 |
| S33P | +C2 + H2-O | 1.4315 | 10940.3797 | 1094.5230 | 1094.6664 | 1094.8097 | 1094.9530 | 1095.0964 | 1095.2397 |

| Variant | Elemental change | Δ m/z | Isotopic Peak Index | | | | | | |
|---|---|---|---|---|---|---|---|---|---|
|  |  |  | 7 | 8 | 9 | 10 | 11 | 12 | 13 |
| R36Q | +O—CH4N2 | −4.0061 | 1089.9454 | 1090.0888 | 1090.2321 | 1090.3754 | 1090.5188 | 1090.6621 | 1090.8054 |
| R55K | —N2 | −4.0009 | 1089.9506 | 1090.0940 | 1090.2373 | 1090.3806 | 1090.5240 | 1090.6673 | 1090.8106 |
| P66A | —C2H2 | −3.7165 | 1090.2350 | 1090.3783 | 1090.5217 | 1090.6650 | 1090.8083 | 1090.9517 | 1091.0950 |
| IGF-1 |  | 0.0000 | 1093.9515 | 1094.0948 | 1094.2382 | 1094.3815 | 1094.5248 | 1094.6682 | 1094.8115 |
| P66T | +O—C | 0.5707 | 1094.5222 | 1094.6655 | 1094.8089 | 1094.9522 | 1095.0955 | 1095.2389 | 1095.3822 |
| T29I | +C2H4—O | 1.7195 | 1095.6710 | 1095.8143 | 1095.9577 | 1096.1010 | 1096.2443 | 1096.3877 | 1096.5310 |
| A67S | +O | 2.2850 | 1096.2365 | 1096.3798 | 1096.5232 | 1096.6665 | 1096.8098 | 1096.9532 | 1097.0965 |
| M59R | +CH3N3—S | 3.5801 | 1097.5316 | 1097.6749 | 1097.8183 | 1097.9616 | 1098.1049 | 1098.2483 | 1098.3916 |
| A70P | +C2H2 | 3.7165 | 1097.6680 | 1097.8114 | 1097.9547 | 1098.0980 | 1098.2414 | 1098.3847 | 1098.5280 |
| S34N | +CHN | 3.8587 | 1097.8102 | 1097.9535 | 1098.0969 | 1098.2402 | 1098.3835 | 1098.5269 | 1098.6702 |
| A38V | +C2H4 | 4.0045 | 1097.9560 | 1098.0993 | 1098.2426 | 1098.3860 | 1098.5299 | 1098.6726 | 1098.8160 |
| r50w | +C5—H2—N2 | 4.2826 | 1098.2341 | 1098.3774 | 1098.5208 | 1098.6641 | 1098.8074 | 1098.9508 | 1099.0941 |
| T4M | +CH2—O | 4.2847 | 1098.2362 | 1098.3795 | 1098.5229 | 1098.6662 | 1098.8095 | 1098.9529 | 1099.0962 |
| A67/70T | +CH2O | 4.2872 | 1098.2387 | 1098.3821 | 1098.5254 | 1098.6687 | 1098.8121 | 1098.9554 | 1099.0987 |
| V17/44M | +S | 4.5674 | 1098.5189 | 1098.6623 | 1098.8056 | 1098.9489 | 1099.0923 | 1099.2356 | 1099.3790 |
| Y31H | —C3—H2 + N2—O | −3.7149 | 1090.2366 | 1090.3799 | 1090.5233 | 1090.6666 | 1090.8099 | 1090.9533 | 1091.0966 |
| S33P | +C2 + H2-O | 1.4315 | 1095.3830 | 1095.5264 | 1095.6697 | 1095.8130 | 1095.9564 | 1096.0997 | 1096.2430 |

TABLE 6-continued

Isotopic Peaks Master Table.
Isotopic Peaks Master Table

| $IP_i$ | m/z | ppm |
|---|---|---|
| $R36Q_4$ | 1089.5154 | 126.8 |
| $P66A_2$ | 1089.5183 | 2.6 |
| $R55K_4$ | 1089.5206 | 2.1 |
| $R36Q_6$ | 1089.6588 | 126.8 |
| $P66A_3$ | 1089.6616 | 2.6 |
| $R55K_5$ | 1089.6640 | 2.1 |
| $R36Q_6$ | 1089.8021 | 126.8 |
| $P66A_4$ | 1089.8050 | 2.6 |
| $R55K_6$ | 1089.8073 | 2.1 |
| $R36Q_7$ | 1089.9454 | 126.7 |
| $P66A_5$ | 1089.9483 | 2.6 |
| $R55K_7$ | 1089.9506 | 2.1 |
| $R36Q_8$ | 1090.0888 | 126.7 |
| $P66A_6$ | 1090.0916 | 2.6 |
| $R55K_8$ | 1090.0940 | 2.1 |
| $R36Q_9$ | 1090.2321 | 126.7 |
| $P66A_7$ | 1090.2350 | 2.6 |
| $R55K_9$ | 1090.2373 | 2.1 |
| $R36Q_{10}$ | 1090.3754 | 126.7 |
| $P66A_8$ | 1090.3783 | 2.6 |
| $R55K_{10}$ | 1090.3806 | 2.1 |
| $R36Q_{11}$ | 1090.5188 | 126.7 |
| $P66A_9$ | 1090.5217 | 2.6 |
| $R55K_{11}$ | 1090.5240 | 2.1 |
| $R36Q_{12}$ | 1090.6621 | 126.7 |
| $P66A_{10}$ | 1090.6650 | 2.6 |
| $R55K_{12}$ | 1090.6673 | 2.1 |
| $R36Q_{13}$ | 1090.8054 | 126.7 |
| $P66A_{11}$ | 1090.8083 | 2.6 |
| $R55K_{13}$ | 1090.8106 | 2.1 |
| $P66A_{12}$ | 1090.9517 | 129.3 |
| $P66A_{13}$ | 1091.0950 | 131.4 |
| $IGF\text{-}I_0$ | 1092.9182 | 1696 |
| $IGF\text{-}I_1$ | 1093.0915 | 131.1 |
| $IGF\text{-}I_2$ | 1093.2348 | 131.1 |
| $IGF\text{-}I_3$ | 1098.3782 | 131.1 |
| $P66T_0$ | 1093.5189 | 128.7 |
| $IGF\text{-}I_4$ | 1093.5215 | 2.4 |
| $P66T_1$ | 1093.6622 | 128.6 |
| $IGF\text{-}I_5$ | 1093.6648 | 2.4 |
| $P66T_2$ | 1093.8055 | 128.6 |
| $IGF\text{-}I_6$ | 1093.8082 | 2.4 |
| $P66T_3$ | 1093.9489 | 128.6 |
| $IGF\text{-}I_7$ | 1093.9515 | 2.4 |
| $P66T_4$ | 1094.0922 | 128.6 |
| $IGF\text{-}I_8$ | 1094.0948 | 2.4 |
| $P66T_5$ | 1094.2355 | 128.6 |
| $IGF\text{-}I_9$ | 1094.2382 | 2.4 |
| $P66T_6$ | 1094.3789 | 128.6 |
| $IGF\text{-}I_{10}$ | 1094.3815 | 2.4 |
| $P66T_7$ | 1094.5222 | 128.5 |
| $IGF\text{-}I_{11}$ | 1094.5248 | 2.4 |
| $P66T_8$ | 1094.6655 | 128.5 |
| $T29I_0$ | 1094.6676 | 1.9 |
| $IGF\text{-}I_{12}$ | 1094.6682 | 0.5 |
| $P66T_9$ | 1094.8089 | 128.5 |
| $T29I_1$ | 1094.8110 | 1.9 |
| $IGF\text{-}I_{13}$ | 1094.8115 | 0.5 |
| $P66T_{10}$ | 1094.9522 | 128.5 |
| $T29I_2$ | 1094.9543 | 1.9 |
| $P66T_{11}$ | 1095.0955 | 129.0 |
| $T29I_3$ | 1095.0976 | 1.9 |
| $A67S_0$ | 1095.2331 | 123.7 |
| $P66T_{12}$ | 1095.2389 | 5.2 |
| $T29I_4$ | 1095.2410 | 1.9 |
| $A67S_1$ | 1095.3765 | 123.7 |
| $P66T_{13}$ | 1095.3822 | 5.2 |
| $I29I_5$ | 1095.3843 | 1.9 |
| $A67S_2$ | 1095.5198 | 123.7 |
| $T29I_6$ | 1095.5276 | 7.1 |
| $A67S_3$ | 1095.6631 | 123.7 |
| $T29I_7$ | 1095.6710 | 7.1 |
| $A67S_4$ | 1095.8065 | 123.7 |
| $T29I_9$ | 1095.8143 | 7.1 |
| $A67S_5$ | 1095.9498 | 123.6 |
| $T29I_9$ | 1095.9577 | 7.1 |
| $A67S_6$ | 1096.0932 | 123.6 |
| $T29I_{10}$ | 1096.1010 | 7.1 |
| $A67S_7$ | 1096.2365 | 123.6 |
| $T29I_{11}$ | 1096.2443 | 7.1 |
| $A67S_8$ | 1096.3798 | 123.6 |
| $T29I_{12}$ | 1096.3877 | 7.1 |
| $A67S_9$ | 1096.5232 | 123.6 |
| $M59R_0$ | 1096.5282 | 4.6 |
| $T29I_{13}$ | 1096.5310 | 2.5 |
| $A70P_0$ | 1096.6647 | 121.9 |
| $A67S_{10}$ | 1096.6665 | 1.7 |
| $M59R_1$ | 1096.6716 | 4.6 |
| $S34N_0$ | 1096.8069 | 123.3 |
| $A70P_1$ | 1096.8080 | 1.1 |
| $A67S_{11}$ | 1096.8098 | 1.7 |
| $M59R_2$ | 1096.8149 | 4.6 |
| $S34N_1$ | 1096.9502 | 123.3 |
| $A70P_2$ | 1096.9513 | 1.1 |
| $A38V_0$ | 1096.9526 | 1.2 |
| $A67S_{12}$ | 1096.9532 | 0.5 |
| $M59R_3$ | 1096.9582 | 4.6 |
| $S34N_2$ | 1097.0935 | 123.3 |
| $A70P_3$ | 1097.0947 | 1.1 |
| $A38V_1$ | 1097.0960 | 1.2 |
| $A67S_{13}$ | 1097.0965 | 0.5 |
| $M59R_4$ | 1097.1016 | 4.6 |
| $R50W_0$ | 1097.2308 | 117.7 |
| $T4M_0$ | 1097.2328 | 1.9 |
| $A67/70T_0$ | 1097.2354 | 2.3 |
| $S34N_3$ | 1097.2369 | 1.4 |
| $A70P_4$ | 1097.2380 | 1.1 |
| $A38V_2$ | 1097.2393 | 1.2 |
| $M59R_5$ | 1097.2449 | 5.1 |
| $R50W_1$ | 1097.3741 | 117.7 |
| $T4M_1$ | 1097.3762. | 1.9 |
| $A67/70T_1$ | 1097.3787 | 2.3 |
| $S34N_4$ | 1097.3802 | 1.4 |
| $A70P_5$ | 1097.3813 | 1.1 |
| $A38V_3$ | 1097.3826 | 1.2 |
| $M59R_6$ | 1097.3883 | 5.1 |
| $V17/44M_0$ | 1097.5156 | 116.0 |
| $R50W_2$ | 1097.5174 | 1.7 |
| $T4M_2$ | 1097.5195 | 1.9 |
| $A67/70T_2$ | 1097.5220 | 2.3 |
| $S34N_5$ | 1097.5235 | 1.4 |
| $A70P_6$ | 1097.5247 | 1.1 |
| $A38V_4$ | 1097.5260 | 1.2 |
| $M59R_7$ | 1097.5316 | 5.1 |
| $V17/44M_1$ | 1097.6589 | 116.0 |
| $R50W_3$ | 1097.6608 | 1.7 |
| $T4M_3$ | 1097.6628 | 1.9 |
| $A67/70T_3$ | 1097.6654 | 2.3 |
| $S34N_6$ | 1097.6669 | 1.4 |
| $A70P_7$ | 1097.6680 | 1.1 |
| $A38V_5$ | 1097.6693 | 1.2 |
| $M59R_8$ | 1097.6749 | 5.1 |
| $V17/44M_2$ | 1097.8023 | 116.0 |
| $R50W_4$ | 1097.8041 | 1.7 |
| $T4M_4$ | 1097.8062 | 1.9 |
| $A67/70T_4$ | 1097.8087 | 2.3 |
| $S34N_7$ | 1097.8102 | 1.4 |
| $A70P_8$ | 1097.8114 | 1.1 |
| $A38V_6$ | 1097.8126 | 1.2 |
| $M59R_9$ | 1097.8183 | 5.1 |
| $V17/44M_8$ | 1097.9456 | 116.0 |
| $R50W_5$ | 1097.9474 | 1.7 |
| $T4M_5$ | 1097.9495 | 1.9 |
| $A67/70T_5$ | 1097.9520 | 2.3 |
| $S34N_8$ | 1097.9535 | 1.4 |
| $A70P_9$ | 1097.9547 | 1.1 |
| $A38V_7$ | 1097.9560 | 1.2 |
| $M59R_{10}$ | 1097.9616 | 5.1 |
| $V17/44M_4$ | 1098.0889 | 116.0 |
| $R50W_6$ | 1098.0908 | 1.7 |

TABLE 6-continued

Isotopic Peaks Master Table.
Isotopic Peaks Master Table

| $IP_i$ | m/z | ppm |
|---|---|---|
| $T4M_6$ | 1098.0929 | 1.9 |
| $A67/70T_6$ | 1098.0954 | 2.3 |
| $S34N_9$ | 1098.0969 | 1.4 |
| $A70P_{10}$ | 1098.0980 | 1.1 |
| $A38V_8$ | 1098.0998 | 1.2 |
| $M59R_{11}$ | 1098.1049 | 5.1 |
| $V17/44M_5$ | 1098.2323 | 115.9 |
| $R50W_7$ | 1098.2341 | 1.7 |
| $T4M_7$ | 1098.2362 | 1.9 |
| $A67/70T_7$ | 1098.2387 | 2.3 |
| $S34N_{10}$ | 1098.2402 | 1.4 |
| $A70P_{11}$ | 1098.2414 | 1.1 |
| $A38V_9$ | 1098.2426 | 1.2 |
| $M59R_{12}$ | 1098.2483 | 5.1 |
| $V17/44M_6$ | 1098.3756 | 115.9 |
| $R50W_8$ | 1098.3774 | 1.7 |
| $T4M_8$ | 1098.3795 | 1.9 |
| $A67/70T_8$ | 1098.3821 | 2.3 |
| $S34N_{11}$ | 1098.3835 | 1.4 |
| $A70P_{12}$ | 1098.3847 | 1.1 |
| $A38V_{10}$ | 1098.3860 | 1.2 |
| $M59R_{13}$ | 1098.3916 | 5.1 |
| $V17/44M_7$ | 1098.5189 | 115.9 |
| $R50W_9$ | 1098.5208 | 1.7 |
| $T4M_9$ | 1098.5229 | 1.9 |
| $A67/70T_9$ | 1098.5254 | 2.3 |
| $S34N_{12}$ | 1098.5269 | 1.4 |
| $A70P_{13}$ | 1098.5280 | 1.1 |
| $A38V_{11}$ | 1098.5293 | 1.2 |
| $V17/44M_8$ | 1098.6623 | 121.0 |
| $R50W_{10}$ | 1098.6641 | 1.7 |
| $T4M_{10}$ | 1098.6662 | 1.9 |
| $A67/70T_{10}$ | 1098.6687 | 2.3 |
| $S34N_{13}$ | 1098.6702 | 1.4 |
| $A38V_{12}$ | 1098.6726 | 2.2 |
| $V17/44M_9$ | 1098.8056 | 121.0 |
| $R50W_{11}$ | 1098.8074 | 1.7 |
| $T4M_{11}$ | 1098.8095 | 1.9 |
| $A67/70T_{11}$ | 1098.8121 | 2.3 |
| $A38V_{13}$ | 1098.8160 | 3.6 |
| $V17/44M_{10}$ | 1098.9489 | 121.0 |
| $R50W_{12}$ | 1098.9508 | 1.7 |
| $T4M_{12}$ | 1098.9529 | 1.9 |
| $A67/70T_{12}$ | 1098.9554 | 2.3 |
| $V17/44M_{11}$ | 1099.0923 | 124.5 |
| $R50W_{13}$ | 1099.0941 | 1.7 |
| $T4M_{13}$ | 1099.0962 | 1.9 |
| $A67/70T_{13}$ | 1099.0987 | 2.3 |
| $V17/44M_{12}$ | 1099.2356 | 124.5 |
| $V17/44M_{13}$ | 1099.3790 | 130.4 |

The theoretical m/z values for all variants were sorted from lowest to highest. Adjacent m/z differences of <10 ppm (pink cells) were then identified and grouped as peaks that cannot be resolved one from another, but that can be resolved from peaks in other groups. In total, 5 m/z values (orange cells) were selected to monitor the WT and 4 variant groups.

TABLE 7

First six y ions for IGF-1 WT, A67T and A70T variants.

| | WT | | A67T | | A70T | |
|---|---|---|---|---|---|---|
| Ion | AA | M/z | AA | M/z | AA | M/z |
| y6 | K | 601.3668 | K | 631.3774 | K | 631.3774 |
| y5 | P | 473.2718 | P | 503.2824 | P | 503.2824 |
| y4 | A | 376.2191 | T | 406.2296 | A | 406.2296 |
| y3 | K | 305.1819 | K | 305.1819 | K | 335.1925 |
| y2 | S | 177.0870 | S | 177.0870 | S | 207.0975 |
| y1 | A | 90.0550 | A | 90.0550 | T | 120.0655 |

Example 2: Sensitive Quantitation of IGF-1 and IGF-2 by Mass Spectrometry

Methodology. The sample is prepared by adding acidified ethanol solution containing the isotopically labeled internal standard and placing in a freezer for 60 minutes. After centrifugation, supernatant is collected and the analyte is extracted and separated by a multiplex High Performance Liquid Chromatography (HPLC) system equipped with an on-line extraction. The detection is carried by an Ion Trap Orbitrap mass spectrometer equipped with an ESI source and operating in a positive All Ion Fragmentation (AIF) mode. The ratio of the analyte response relative to that of the internal standard is used to build a calibration curve and to quantify IGF-1 or IGF-2 in patient samples.

TABLE 8

Mass/charge ratios of IGF-1 and IGF-2 ions

| | m/z | |
|---|---|---|
| Ion | Current | Alternative |
| IGF-1 | | |
| Quantitation peak | 1093.5215 | 1093.6648 |
| Confirming peak 1 | 1093.6648 | 1093.5215 |
| Confirming peak 2 | 1093.3782 | 1093.8082 |
| Internal Standard | 1106.7670 | |
| IGF-2 | | |
| Quantitation peak | 1067.9391 | |
| Confirming peak 1 | 1067.7958 | |
| Confirming peak 2 | 1068.0824 | |
| Internal Standard | 1106.7670 | |

Precision Studies. Definition: Reproducibility of a sample within an assay.

Conventional Technologies: acceptability criteria: SD<TEa/3; each process Sigma based on SD and CV % has to be >3.0.

Advanced Technologies: acceptability criteria will be determined by the Medical and Scientific Director(s) overseeing the assay. Acceptance criteria should be data based, rational and defendable.

Within Run Precision. Acceptability criteria: The SD should be less than allowable SD (wr) or ≤TEa/4.

The intra-assay precision is defined as the reproducibility of a quality control pool within an assay. All levels of QC were analyzed to determine the mean, SD and coefficient of variation (% CV). Each level was measured 5 times per run over 5 runs for a total of 25 replicates. The summary data for the analytes is shown below. Original data are listed in tables below.

TABLE 9

| Summary IGF-1 | Level 1 | Level 2 | Level 3 | Level 4 |
|---|---|---|---|---|
| Total Count | 25 | 25 | 25 | 25 |
| Avg. Grand Mean, ng/mL | 41.46 | 146.22 | 294.35 | 104.28 |
| Avg. within run SD, ng/mL | 2.924 | 6.231 | 10.439 | 3.920 |
| Avg. within run CV | 7.05% | 4.26% | 3.55% | 3.76% |

TABLE 10

| Summary IGF-2 | Level 1 | Level 2 | Level 3 |
|---|---|---|---|
| Total Count | 25 | 25 | 25 |
| Avg. Grand Mean, ng/mL | 150.90 | 557.99 | 1055.81 |
| Avg. within run SD, ng/mL | 4.880 | 13.063 | 35.942 |
| Avg. within run CV | 3.23% | 2.34% | 3.40% |

The results indicate that acceptability criteria were met for the detection of IGF-1 and IGF-2 in Human Serum.

Total Precision. Acceptability criteria: unacceptable if Total SD≥1/2TEa or Total SD must be less than a defined maximum SD or CV.

The inter-assay precision is defined as the reproducibility of a sample between assays. All levels of QC were analyzed to determine the mean, SD and coefficient of variation (% CV). Each level was measured 2 times per day over 20 days for a total of 40 replicates. The summary data from the analyte are shown below. Original data are listed in tables below.

TABLE 11

| Summary IGF-1 | Level 1 | Level 2 | Level 3 | Level 4 |
|---|---|---|---|---|
| Count | 40 | 40 | 40 | 40 |
| Grand Mean, ng/mL | 40.45 | 176.65 | 357.68 | 64.60 |
| Overall SD, ng/mL | 3.56 | 11.36 | 21.37 | 4.81 |
| Overall CV | 8.79% | 6.43% | 5.97% | 7.45% |
| Sigma Overall | 3.41 | 4.67 | 5.02 | 4.03 |
| Precision >= 3.0 sigma? | YES | YES | YES | YES |

TABLE 12

| Summary IGF-2 | Level 1 | Level 2 | Level 3 |
|---|---|---|---|
| Count | 40 | 40 | 40 |
| Grand Mean, ng/mL | 175.45 | 545.37 | 1145.03 |
| Overall SD, ng/mL | 11.18 | 38.33 | 65.32 |
| Overall CV | 6.37% | 7.03% | 5.71% |
| Sigma Overall | 4.71 | 4.27 | 5.26 |
| Precision >= 3.0 sigma? | YES | YES | YES |

The results indicate that acceptability criteria were met for the detection of IGF-1 and IGF-2 in Human Serum.

Limit of Blank (LOB). LOB was determined as the mean+2SD of the zero calibrator. LOB is 1.621 ng/mL and 10.162 ng/mL for IGF-1 and IGF-2, respectively.

Limit of Detection (LOD). LOD was determined as the mean+4SD of the zero calibrator. LOD is 2.446 ng/mL and 12.276 ng/mL for IGF-1 and IGF-2, respectively.

Limit of Quantitation (LOQ). Acceptability criteria: The lowest concentration at which SD<TEa/3.

Three pools, prepared using standard calibrator material in methanol spiked to stripped urine, were tested to determine the LOQ. Each pool was measured 5 times per run, over 5 runs. The LOQ was determined by the lowest concentration at which SD<TEa/3. The summary data for the Detection Limits are shown below. LOQ is 7.794 ng/mL and 31.983 ng/mL for IGF-1 and IGF-2, respectively.

TABLE 13

| Count IGF-1 | 25 | 25 | 25 | 25 |
|---|---|---|---|---|
| Mean, ng/mL | 7.794 | 15.818 | 32.331 | 0.796 |
| SD, ng/mL | 0.308 | 0.972 | 2.098 | 0.412 |
| TEa/3 | 0.779 | 1.582 | 3.233 | |
| Is SD < TEa/3 ? | YES | YES | YES | |
| Is Mean >= LOD ? | YES | YES | YES | |
| Limit of Blank (LOB), ng/mL | | | | 1.621 |
| Limit of Detection (LOD), ng/mL | | | | 2.446 |
| Limit of Quantitation (LOQ), ng/mL | | | | 7.794 |

TABLE 14

| Count IGF-2 | 25 | 25 | 25 | 25 |
|---|---|---|---|---|
| Mean, ng/mL | 31.983 | 60.508 | 119.335 | 8.049 |
| SD, ng/mL | 1.286 | 2.632 | 5.031 | 1.057 |
| TEa/3 | 3.198 | 6.051 | 11.933 | |
| Is SD < TEa/3 ? | YES | YES | YES | |
| Is Mean >= LOD ? | YES | YES | YES | |
| Limit of Blank (LOB), ng/mL | | | | 10.162 |
| Limit of Detection (LOD), ng/mL | | | | 12.276 |
| Limit of Quantitation (LOQ), ng/mL | | | | 31.983 |

Calibration Verification. Acceptability criteria: the average of the observed values should deviate from the expected range by no more than TEa/4.

The linearity of the assay was determined by analyzing results of 2 different calibrator lots. A calibrator lot was freshly prepared and tested as unknowns against the current working calibrators (previous preparation). The difference between the targeted concentrations and observed concentrations was analyzed. Statistics performed on the data indicate acceptable performance.

The Analytical Measurement Range (AMR) is 7.8-2,000 ng/mL and 31.3-2,000 ng/mL for IGF-1 and IGF-2, respectively.

Reportable Range (RR). The Clinical Reportable Range (CRR) is 7.8-2,000 ng/mL and 31.3-2,000 ng/mL for IGF-1 and IGF-2, respectively.

Six (6) patient samples with known concentrations of IGF-1 were diluted 2, 4, 8 and 16 fold with stripped serum. Recoveries at 2, 4, and 8 dilution levels were within 100±20% of recovery error.

Six (6) patient samples with known concentrations of IGF-2 were diluted 2, 4, 8 and 16 fold with stripped serum. All recoveries at each dilution level were within 100±20% of recovery error.

Recovery Study. Acceptability criteria: the error due to lack of perfect recovery (amount recovered MINUS amount added) should be ≤TEa for each individual measurement.

Spike recovery study was executed to evaluate any matrix effect within the assay. For IGF-1 base recovery samples (six in total) were prepared by combining 200 uL of stripped serum with 400 uL of each sample. Spiked samples were prepared by adding 200 uL of the 2,000 ng/mL stock solution of IGF-1 to 400 uL of each sample. The results are within the acceptable accuracy range.

For IGF-2 base recovery samples (six in total) were prepared by combining 100 uL of stripped serum with 100 uL of each sample. Spiked samples were prepared by adding 100 uL of the 2000 ng/mL stock solution of IGF-2 to 100 uL of each sample. The results are within the acceptable accuracy range.

Split-Sample Comparison Study. Acceptability criteria: The absolute value of difference in averages should be less then TEa/4.

RIA vs. current Agilent TOF LC-MS. The split-sample comparison studies were conducted comparing the Radioimmunoassay (RIA) and current Agilent TOF LC-MS techniques for the IGF-1 quantitation. Samples from 100 patients were split and analyzed with LC-MS method on the Aria TX-4 system. Samples were simultaneously assayed using RIA methodologies at Esoterix Laboratory (Calabasas, CA). (Test Code #500282; blocking RIA after acid: alcohol extraction). Data were analyzed by Deming regression; n=100, m=1.039±0.01572, b=−11.55±5.673. The LC-MS method was found to have excellent agreement with the RIA.

HPLC-MS method comparison. A split-sample comparison of IGF-1 by LC-MS was conducted between the current Agilent TOF and a proposed Q Exactive Focus HPLC-MS method. One hundred ninety seven (n=197) patient samples were tested and linear regression was 1.0266x+0.57; $r^2$=0.9861. The results indicate that acceptability criteria were met for the quantitation of IGF-1 in Human Serum.

A split-sample comparison of IGF-2 by LC-MS was conducted between the current and a proposed HPLC-MS method. Two hundred fourteen (n=144) patient samples were tested and linear regression was 0.9327x+38.17; $r^2$=0.9132.

Measurement Uncertainty. Definition: Degree to which one is certain of a result of a particular measurement. Expressed as the $95^{th}$ percentile confidence interval around a given number determined by the mean+/−1.96*SD of multiple determinations.

For modified or unmodified FDA Cleared or Approved tests, measurement uncertainty is determined by measuring each QC level 5 times per day for 5 separate days. If it is necessary to complete the MU study over a shorter time frame than 5 separate days, each set of 5 QC values must be in separate runs and an acknowledgement of the shortened time-frame documented in the final precision study.

MU Confidence Intervals are calculated using the Precision sheet of the Assay Validation Calculator template. Analyze data by calculating the mean and standard deviation, the MU is then calculated by multiplying the SD by 1.96 and adding or subtracting this to the mean.

The confidence intervals for each QC level of IGF-1 and IGF-2 in Human Serum is provided in the table below.

TABLE 15

| Summary IGF-1 | Level 1 | Level 2 | Level 3 | Level 4 |
| --- | --- | --- | --- | --- |
| Count | 25 | 25 | 25 | 25 |
| Grand Mean, ng/mL | 41.46 | 146.22 | 294.35 | 104.28 |
| Overall SD, ng/mL | 2.76 | 7.86 | 12.04 | 4.49 |
| Overall CV | 6.65% | 5.38% | 4.09% | 4.30% |
| Measurement Uncertainty Lower 95&ile CI | 36.06 | 130.82 | 270.76 | 95.48 |
| Measurement Uncertainty Higher 95&ile CI | 46.87 | 161.63 | 317.94 | 113.07 |

TABLE 16

| Summary IGF-2 | Level 1 | Level 2 | Level 3 |
| --- | --- | --- | --- |
| Count | 25 | 25 | 25 |
| Grand Mean, ng/mL | 150.90 | 557.99 | 1055.81 |
| Overall SD, ng/mL | 4.98 | 23.76 | 57.00 |
| Overall CV | 3.30% | 4.26% | 5.40% |
| Measurement Uncertainty Lower 95&ile CI | 141.13 | 511.41 | 944.09 |
| Measurement Uncertainty Higher 95&ile CI | 160.67 | 604.56 | 1167.53 |

Specimen Stability. Acceptability criteria: A sample is considered stable as long as the % difference between the baseline value and the time/temperature sample value is ≤TEa for that analyte. The serum pools were obtained from Clinical Correlations Department and were pre-aliquoted and ready for set-up.

To study IGF-1 and IGF-2 recovery at various temperatures, ten samples for each were evaluated. From each pool, aliquots were incubated at various temperatures for the times indicated in Tables 7-11. When a stability study pool reaches the appropriate incubation time, it is placed into the −90° C. to −60° C. freezer until the day of assay at which time all study pools are assayed together.

Freeze/thaw Stability. Six samples evaluated for freeze/thaw recovery of IGF-1 materials in human serum. All pools were then put into aliquots and stored at −90° C. to −60° C. Six aliquots from each pool underwent a different number of freeze/thaw cycles (0-5). The data in Table 7a indicates that 5 additional freeze/thaw cycles from the initial freeze/thaw (cycle "0") for all pools tested, retained acceptable levels of activity for IGF-1 in human serum The initial freeze/thaw cycle (cycle "0") represents the freeze/thaw all specimens will undergo during the collection process. The recovery of the IGF-2 in patient samples was performed in a similar way for up to 5 freeze-thaw cycles.

IGF-1 patient samples are stable for at least 6 freeze-thaw cycles. IGF-2 patient samples are stable for at least 5 freeze-thaw cycles.

Refrigerated Stability (2.0° C. to 8.0° C.). The data shows that human serum retained acceptable levels of IGF-1 and IGF-2 activities at refrigerated temperatures for at least 7 days.

Ambient Stability (18.0° C. to 25.0° C.). The data shows that human serum retained acceptable levels of IGF-1 and IGF-2 activities at room temperature for at least 2 and at least 7 days, respectively.

Frozen Stability (−30.0° C. to −10.0° C.). The data shows that human serum retained acceptable levels of IGF-1 and IGF-2 activities at frozen temperature for at least 2 months and at least 21 days, respectively.

Frozen Stability: Ultralow (−90.0° C. to −60.0° C.). The data shows that human serum retained acceptable levels of IGF-1 and IGF-2 activities at room temperature for at least 3 months and at least 34 days, respectively.

Interference Study. Acceptability criteria: The mean difference due to a potential interfering substance should be ≤TEa/4 to be considered acceptable.

Hemolysis Interference. The effects of hemolysis in the assay were evaluated by spiking three patient samples (100 uL) with hemolyzed RBCs at low, medium, and high concentrations to represent slight, moderate, and gross hemolysis.

For IGF-1 the average recoveries were 82.4%, 72.4%, and 63.9% for slight, moderate, and gross hemolysis, respectively. Slight hemolysis does not interfere with IGF-1 in Serum assay, while moderate and gross hemolytic samples are unacceptable.

For IGF-2 the average recoveries were 111.9%, 119.6%, and 130.1% for slight, moderate, and gross hemolysis, respectively. While the average recoveries for slight and moderate hemolysis are within acceptable range, the individual values are not. Hemolysis interferes with IGF-2 in Serum assay at all levels. Samples with any degree of hemolysis are not acceptable.

Lipemia Interference. The effects of lipemia in the assay were evaluated by spiking three patient samples (100 uL)

with Intralipid (20%, emulsion) at low, medium, and high concentrations to represent slight, moderate, and gross lipemia.

For IGF-1 the average recoveries were 102.8%, 97.0%, and 96.8% for slight, moderate, and gross lipemia, respectively. Lipemia does not interfere with IGF-1 in Serum assay. Samples with any degree of lipemia are acceptable.

For IGF-2 the average recoveries were 105.1%, 108.6%, and 122.5% for slight, moderate, and gross lipemia, respectively. Lipemia does not interfere with IGF-2 in Serum assay at light and moderate levels. Samples with gross lipemia are not acceptable.

Bilirubin Interference. The effects of icterus in the assay were evaluated by spiking three patient samples (100 uL) with Bilirubin powder at low, medium, and high concentrations to represent slight, moderate, and gross icterus.

For IGF-1 the average recoveries were 102.8%, 99.0%, and 98.9% for slight, moderate, and gross icterus, respectively. Icterus does not interfere with IGF-1 in Serum assay. Samples with any degree of icterus are acceptable.

For IGF-2 the average recoveries were 99.7%, 102.0%, and 106.0% for slight, moderate, and gross icterus, respectively. Icterus does not interfere with IGF-2 in Serum assay. Samples with any degree of icterus are acceptable.

Analytical Specificity. The interference of IGF-1 binding protein was also tested using the mixture that contained the following compounds: IGF Binding protein 1 (IGFBP1), IGF Binding protein 2 (IGFBP2) and IGF Binding protein 3 (IGFBP3).

Six patient samples were collected and run to establish a baseline. Equal volumes (200 uL) of each sample and Binding proteins (800 ng/mL of IGFBP1, 2,000 ng/mL of IGFBP2 and 10,000 ng/mL of IGFBP3) was then combined and tested to calculate the IGF-1 recovery. After these, six solutions of the mixture of Binding proteins (same concentrations as before) were run. The results indicate that the recoveries were within 100±20% and the acceptability criteria were met for the quantitation of IGF-1 in Human Serum. The sample recovery indicated that no interference was present.

One patient samples was collected and run to establish a baseline. Equal volumes (200 uL) of the sample and Binding proteins (800 ng/mL of IGFBP1, 2,000 ng/mL of IGFBP2 and 10,000 ng/mL of IGFBP3) was then combined and tested to calculate the IGF-2 recovery. After these, a solution of the mixture of Binding proteins (same concentrations as before) was run. The results indicate that the recoveries were within 100±20% and the acceptability criteria were met for the quantitation of IGF-2 in Human Serum. The sample recovery indicated that no interference was present. NOTE: the low signal of IGF-2 in the binding proteins solution can be explained by the low amount of IGF-2 present in the stripped serum used as the matrix.

Ion Suppression Study. The purpose of this study was to determine if any ion suppression or ion enhancement effects are observed at the course of the gradient or at the injection of matrix components. To assess this, a post-column "T" infusion of an isotope labeled internal standard (N15 labeled IGF-1) during the acquisition of patient samples (6 males and 6 females) was performed. In this experiment the total ion count (TIC) showed change of less than 20% during the elution time of the analyte of interest. The test indicates that the assay has passed the test and no ion suppression was observed for both, IGF-1 and IGF-2.

Carryover. Twelve replicates of the blank serum were tested immediately after eight replicates of the high concentration standard (2,000 ng/mL) and carryover was evaluated in each LC column (corresponding to each of the 4-channel Aria LC system). The low calibrator replicates exhibited no carry over for both, IGF-1 and IGF-2 in human Serum. Reference Interval (RI).

TABLE 17

Pediatric Reference Ranges for IGF-1:

| Age(Years) | Females ng/mL | Males ng/mL |
|---|---|---|
| <1* | 17-185 | 14-142 |
| 1-1.9* | 15-175 | 12-134 |
| 2-2.9* | 16-179 | 12-135 |
| 3-3.9 | 38-214 | 30-155 |
| 4-4.9 | 34-238 | 28-181 |
| 5-5.9 | 37-272 | 31-214 |
| 6-6.9 | 45-316 | 38-253 |
| 7-7.9 | 58-367 | 48-298 |
| 8-8.9 | 76-424 | 62-347 |
| 9-9.9 | 99-483 | 80-398 |
| 10-10.9 | 125-541 | 100-449 |
| 11-11.9 | 152-593 | 123-497 |
| 12-12.9 | 178-636 | 146-541 |
| 13-13.9 | 200-664 | 168-576 |
| 14-14.9 | 214-673 | 187-599 |
| 15-15.9 | 218-659 | 201-609 |
| 16-16.9 | 208-619 | 209-602 |
| 17-17.9 | 185-551 | 207-576 |

TABLE 18

Females Tanner Stage

| Age(Years) | Tanner Stage* 1 ng/mL | Tanner Stage* 2 ng/mL | Tanner Stage* 3 ng/mL | Tanner Stage* 4, 5 ng/mL |
|---|---|---|---|---|
| 8-8.9 | 80-307 | 84-414 | 197-642 | 388-871 |
| 9-9.9 | 92-332 | 91-432 | 197-642 | 358-823 |
| 10-10.9 | 105-359 | 99-451 | 197-642 | 330-776 |
| 11-11.9 | 118-387 | 107-470 | 197-642 | 304-731 |
| 12-12.9 | 133-416 | 115-490 | 197-642 | 278-688 |
| 13-13.9 | 148-447 | 123-510 | 197-642 | 254-646 |

*Tanner Stage based on Breast Stage

TABLE 19

Male Tanner Stage

| Age(Years) | Tanner Stage* 1 ng/mL | Tanner Stage* 2, 3 ng/mL | Tanner Stage* 4, 5 ng/mL |
|---|---|---|---|
| 10-10.9 | 84-315 | 78-418 | 349-817 |
| 11-11.9 | 96-341 | 101-478 | 318-765 |
| 12-12.9 | 109-368 | 127-543 | 289-716 |
| 13-13.9 | 123-396 | 158-614 | 262-668 |
| 14-14.9 | 138-426 | 192-689 | 236-622 |
| 15-15.9 | 153-457 | 230-769 | 212-578 |

*Tanner Stage based on Testicular Volume

TABLE 20

Adult Reference Ranges for IGF-1, Males & Females:

| Age(Years) | ng/mL |
|---|---|
| 18-19.9 | 108-548 |
| 20-24.9 | 83-456 |
| 25-29.9 | 63-373 |
| 30-39.9 | 53-331 |
| 40-49.9 | 52-328 |
| 50-59.9 | 50-317 |

TABLE 20-continued

| Adult Reference Ranges for IGF-1, Males & Females: | |
|---|---|
| 60-69.9 | 41-279 |
| 70-79.9 | 34-245 |
| >80 | 34-246 |

| | |
|---|---|
| Z-Score (Male): | −2.0-+2.0 SD |
| Z-Score (Female): | −2.0-+2.0 SD |
| Reference Ranges for IGF-2 | |
| Adults, Males and Females | 267-616 ng/mL |
| Pediatric, Males and Females (Ages 2-18 years) | 260-630 ng/mL |

Specimen Type/Alternate Specimen Types. The IGF-1 assay is validated for human serum collected in red top (no gel) tubes. Pairwise comparison of IGF-1 from SST tubes versus red top tubes was completed. The acceptability criterion was met for the SST tubes.

The IGF-2 assay is validated for human serum collected in red top tubes. Forty subjects, with paired red-top and SST samples, were collected and analyzed for IGF-2. SST serum versus red top serum was compared. No significant differences between sample tube types were observed. The acceptability criterion was met for the SST tubes.

TABLE 21

| Comparison | (n) | Slope | Y-intercept | $R^2$ |
|---|---|---|---|---|
| Linear Regression | 40 | 0.947 | 22.3 | 1 |
| Deming Regression | 40 | 0.99 | 5.27 | |

It was previously noted that plasma samples exhibited viscosity incompatible with the automated pipetting system. For this reason, plasma samples are not acceptable for IGF-1 and IGF-2 assays.

Clinical Utility. IGF-1 and IGF-2 measurements are useful in the diagnosis of growth disorders. Dwarfism is associated with decreased levels of serum IGF-1 and IGF-2 while acromegaly results in high levels of serum IGF-1 and IGF-2.

Deviations. In IGF-2 assay split sample comparison there is one point SE (20.21)>TEa/4 (20.03) but <TEa/3 (26.70). SE less than TEa/4 is preferable and SE less than TEa/3 is acceptable for these comparison.

Conclusions. This validation study has been reviewed and the performance of the method is considered acceptable for patient testing.

TABLE 22

Summary of Validation Results

| Specimen Type | | Human Serum | | | | |
|---|---|---|---|---|---|---|
| | Summary IGF-1 | | Level 1 | Level 2 | Level 3 | Level 4 |
| Intra Assay Precision | Within run SD, ng/mL | | 2.924 | 6.231 | 10.439 | 3.920 |
| | Within run CV | | 7.05% | 4.26% | 3.55% | 3.76% |
| | Summary IGF-2 | | Level 1 | Level 2 | Level 3 | |
| | Within run SD, ng/mL | | 4.880 | 13.063 | 35.942 | |
| | Within run CV | | 3.23% | 2.34% | 3.40% | |
| | Summary IGF-1 | | Level 1 | Level 2 | Level 3 | Level 4 |
| Inter Assay Precision | Overall SD, ng/mL | | 3.56 | 11.36 | 21.37 | 4.81 |
| | Overall CV | | 8.79% | 6.43% | 5.97% | 7.45% |
| | Summary IGF-2 | | Level 1 | Level 2 | Level 3 | |
| | Overall SD, ng/mL | | 11.18 | 38.33 | 65.32 | |
| | Overall CV | | 6.37% | 7.03% | 5.71% | |
| Method Comparison | Split sample comparison studies: 1) IGF-1 current and proposed HPLC-MS: Linear regression was 1.0266x + 0.57; $r^2 = 0.9861$. 2) IGF-2 current and proposed HPLC-MS: Linear regression was 0.8639x + 59.81; $r^2 = 0.9291$. | | | | | |
| Recovery Study | IGF-1 and IGF-2 recovery bias was acceptable. | | | | | |

| | | IGF-1 | IGF-2 |
|---|---|---|---|
| Analytical Sensitivity (Limit of Detection and Limit of Quantitation) | Limit of Blank (LOB), ng/mL | 1.621 | 10.162 |
| | Limit of Detection (LOD), ng/mL | 2.446 | 12.276 |
| | Limit of Quantitation (LOQ), ng/mL | 7.794 | 31.983 |

| | |
|---|---|
| Analytical Specificity (Cross Reactivity) | No cross reactivity was detected |
| Analytical Specificity (Interference) | For IGF-1 samples with any degree of hemolysis, icterus and lipemia are acceptable. For IGF-2 samples with any degree of hemolysis and high degree of lipemia are not acceptable. No chemical interference was detected. |
| Linearity | For IGF-1 linear range of 7.8-2,000 ng/mL was verified. For IGF-2 linear range of 31.3-2,000 ng/mL was verified. |
| Analytical Measurement Range (AMR) | For IGF-1 AMR is 7.8-2,000 ng/mL. For IGF-2 AMR is 31.3-2,000 ng/mL. |
| Reportable Range (RR) | For IGF-1 RR is 7.8-2,000 ng/mL. For IGF-2 RR is 31.3-2,000 ng/mL. |
| Reference Interval (RI) | See Section 14 and Memos in the Appendix II. |
| Carryover | No carry over was observed for these assays. |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for detecting insulin-like growth factor-I (IGF-I) in a sample, the method comprising:
   a. ionizing IGF-I in the sample to produce one or more ions detectable by mass spectrometry;
   b. detecting one or more of the ions comprising an ion with a mass-to-charge ratio selected from the group consisting of 1089.8±0.5, 1095±0.5, 1097.09±0.5, and 1098.09±0.5 by mass spectrometry; and
   c. using the detected ion or ions to determine the presence of IGF-I variant(s) in the sample.

2. The method of claim 1, wherein the detection of m/z 1089.8±0.5 determines the presence of $P66A_4$, $R55K_6$, or $R36Q_6$.

3. The method of claim 1, wherein the detection of m/z 1095±0.5 determines the presence of $A67S_4$ or $T29I_8$.

4. The method of claim 1, wherein the detection of m/z 1097.09±0.5 determines the presence of $S34N_2$, $A70P_3$, $A38V_1$, $M59R_4$, or $A67S_{13}$.

5. The method of claim 1, wherein the detection of m/z 1098.09+0.5 determines the presence of $S34N_9$, $A70P_{10}$, $A38V_8$, $M59R_{11}$, $V17/44M_4$, $R50W_6$, $T4M_6$, or $A67/70T_6$.

6. The method of claim 1, further comprising purifying the protein by high performance liquid chromatography (HPLC) prior to ionization.

7. The method of claim 1, wherein the sample comprises plasma or serum.

* * * * *